(12) United States Patent
Nelson et al.

(10) Patent No.: US 9,777,319 B2
(45) Date of Patent: Oct. 3, 2017

(54) METHOD FOR ISOTHERMAL DNA AMPLIFICATION STARTING FROM AN RNA TEMPLATE

(75) Inventors: John Richard Nelson, Clifton Park, NY (US); Robert Scott Duthie, Schenectady, NY (US); Gregory Andrew Grossmann, Halfmoon, NY (US); Ryan Charles Heller, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 380 days.

(21) Appl. No.: 13/538,955

(22) Filed: Jun. 29, 2012

(65) Prior Publication Data

US 2014/0004508 A1 Jan. 2, 2014

(51) Int. Cl.
*C12Q 1/68* (2006.01)

(52) U.S. Cl.
CPC .................. *C12Q 1/6865* (2013.01)

(58) Field of Classification Search
None
See application file for complete search history.

(56) References Cited

U.S. PATENT DOCUMENTS

| | | |
|---|---|---|
| 5,536,649 A | 7/1996 | Fraiser et al. |
| 5,744,312 A | 4/1998 | Mamone et al. |
| 5,807,669 A * | 9/1998 | Schupbach ............. C12Q 1/48 435/4 |
| 5,866,336 A | 2/1999 | Nazarenko et al. |
| 6,323,009 B1 | 11/2001 | Lasken et al. |
| 6,379,940 B2 | 4/2002 | Moffett et al. |
| 6,951,722 B2 | 10/2005 | Mukai et al. |
| 7,198,894 B2 | 4/2007 | Barany et al. |
| 7,294,461 B2 | 11/2007 | Kurn |

(Continued)

FOREIGN PATENT DOCUMENTS

| | | |
|---|---|---|
| EP | 0585660 B1 | 5/2000 |
| EP | 1167524 A1 | 1/2002 |

(Continued)

OTHER PUBLICATIONS

Nuovo et al. (2000) Diagnostic Molecular Pathology 9 (4): 195-202.*

(Continued)

*Primary Examiner* — Young J Kim
(74) *Attorney, Agent, or Firm* — Pabitra K. Chakrabarti

(57) ABSTRACT

A method of amplifying RNA template is provided. The method comprises reverse-transcribing a ribonucleic acid (RNA) template to form a cDNA using a first reaction mixture comprising RNA template, at least one primer capable of hybridizing to the RNA template, a reverse transcriptase and deoxynucleoside triphosphates (dNTPs); and amplifying the cDNA to form an amplified product using a second reaction mixture comprising at least one strand displacement DNA polymerase, at least one inosine-containing primer and a nuclease that is capable of nicking DNA 3' to an inosine residue of the primer. The method is accomplished under an isothermal condition without denaturing the cDNA template. A method of quantifying RNA template in a sample and a method of detecting RNA template in a sample are also provided.

22 Claims, 7 Drawing Sheets

(56) References Cited

U.S. PATENT DOCUMENTS

| | | | |
|---|---|---|---|
| 7,309,571 | B2 | 12/2007 | Nelson |
| 7,579,153 | B2 | 8/2009 | Brenner et al. |
| 7,662,594 | B2 | 2/2010 | Kong et al. |
| 7,700,282 | B2 | 4/2010 | Tetzner et al. |
| 7,888,018 | B2 * | 2/2011 | Getts .................... C12Q 1/6853 435/5 |
| 8,202,972 | B2 | 6/2012 | Nelson et al. |
| 2001/0041334 | A1 | 11/2001 | Rashtchian et al. |
| 2003/0104431 | A1 | 6/2003 | Van Ness et al. |
| 2003/0124576 | A1 | 7/2003 | Kumar et al. |
| 2003/0157533 | A1 | 8/2003 | Davis et al. |
| 2003/0228620 | A1 | 12/2003 | Du Breuil Lastrucci |
| 2004/0067559 | A1 | 4/2004 | McCarthy et al. |
| 2004/0180372 | A1 | 9/2004 | Nelson |
| 2005/0026147 | A1 | 2/2005 | Walker et al. |
| 2006/0188893 | A1 | 8/2006 | Kumar et al. |
| 2007/0020639 | A1 | 1/2007 | Shapero |
| 2007/0148636 | A1 | 6/2007 | Song et al. |
| 2008/0055742 | A1 | 3/2008 | Sato |
| 2009/0011472 | A1 * | 1/2009 | Nelson et al. ............. 435/91.53 |
| 2009/0047678 | A1 | 2/2009 | Kutyavin |
| 2009/0155859 | A1 | 6/2009 | Nelson et al. |
| 2010/0021973 | A1 | 1/2010 | Makarov et al. |
| 2010/0055742 | A1 | 3/2010 | Nakashima et al. |
| 2010/0221785 | A1 | 9/2010 | Millar et al. |
| 2010/0311058 | A1 | 12/2010 | Kim et al. |
| 2011/0171649 | A1 | 7/2011 | Kutyavin |
| 2011/0195457 | A1 | 8/2011 | Nelson et al. |
| 2012/0021461 | A1 | 1/2012 | Millar et al. |

FOREIGN PATENT DOCUMENTS

| | | | | |
|---|---|---|---|---|
| EP | 2330214 | A1 | 6/2011 | |
| JP | 2007325568 | A | 12/2007 | |
| WO | 2004003232 | A1 | 1/2004 | |
| WO | 2008143627 | A2 | 11/2008 | |
| WO | WO 2010/083561 | A1 * | 7/2010 | ............. C12N 15/10 |
| WO | 2014164479 | A1 | 10/2014 | |

OTHER PUBLICATIONS

Elisabeth Lehmann et al.; "Molecular Basis of RNA-dependent RNA polymerase II activity"; © 2007 Nature PublishingGroup; 5 Pages.
Search Report and Written Opinion from corresponding PCT Application No. PCT/US2013/48229 dated Mar. 3, 2014.
Zhu et al., "The Use of Exonuclease III for Polymerase Chain Reaction Sterilization", Nucleic Acid Research, vol. No. 19, Issue No. 9, pp. 2511, Jan. 28, 1991.
Li et al., "Eliminating Primers from Completed Polymerase Chain Reactions With Exonuclease VII", Nucleic Acid Research, vol. No. 19, Issue No. 11, pp. 3139-3141, Jun. 11, 1991.
Walker et al., "Isothermal in Vitro Amplification of DNA by a Restriction Enzyme/DNA Polymerase System", Proc. Nati. Acad. Sci. USA, Applied Biological Sciences, vol. No. 89, pp. 392-396, Jan. 1992.
Yao et al., "Purification and Characterization of a Novel Deoxyinosine-specific Enzyme, Deoxyinosine 3' Endonuclease, from Escherichia coli", The Journal of Biological Chemistry, vol. No. 269, Issue No. 23, pp. 16260-16268, Jan. 7, 1994.
Yao et al., "Interaction of Deoxyinosine 3'-Endonuclease from Escherichia coli with DNA Containing Deoxyinosine", The Journal of Biological Chemistry, vol. No. 270, Issue No. 48, pp. 28609-28616, Apr. 25, 1995.
Yao et al., "Further Characterization of Escherichia coli Endonuclease V—Mechanism of Recognition for Deoxyinosine, Deoxyuridine, and Base Mismatches in DNA", The Journal of Biological Chemistry, vol. No. 272, Issue No. 49, pp. 30774-30779, Dec. 5, 1997.
Liu et al., "A Deoxyinosine Specific Endonuclease from Hyperthemophile, Archaeoglobus Fulgidus: a Homolog of Escherichia coli Endonuclease V", Mutation Research, vol. No. 461, pp. 169-177, Jun. 2, 2000.
Huang et al., "Multiple Cleavage Activities of Endonuclease V from Thermotoga Maritima: Recognition and Strand Nicking Mechanism", Biochemistry, vol. No. 40, pp. 8738-8748, Jan. 29, 2001.
Huang et al., "Mutational Analysis of Endonuclease V from Thermotoga Maritima", Biochemistry, vol. No. 41, Issue No. 26, pp. 8342-8350, Apr. 28, 2002.
Moe et al., "Incision at Hypoxanthine Residues in DNA by a Mammalian Homologue of the Escherichia coli Antimutator Enzyme Endonuclease V", Nucleic Acids Research, vol. No. 31, Issue No. 14, pp. 3893-38900, Apr. 24, 2003.
Vincent et al., "Helicase-Dependent Isothermal DNA Amplification", European Molecular Biology Organization Reports, vol. No. 5, Issue No. 8, pp. 795-800, Aug. 2004.
Hitchcock et al., "Cleavage of Deoxyoxanosine-Containing Oligodeoxyribonucleotides by Bacterial Endonuclease V", Nucleic Acids Research, vol. No. 32, Issue No. 13, pp. 4071-4080, Aug. 2, 2004.
Feng et al., "Defining Amino Acid Residues Involved in DNA-Protein Interactions and Revelation of 3'-Exonuclease Activity in Endonuclease V",Biochemistry, vol. No. 44, pp. 11486-11495, May 5, 2005.
Feng et al., "Active Site Plasticity of Endonuclease V from Salmonella typhimurium", Biochemistry, vol. No. 44, pp. 675-683, 2005.
Feng et al., "Catalytic Mechanism of Endonuclease V: A Catalytic and Regulatory Two-Metal Model", Biochemistry, vol. No. 45, pp. 10251-10259, Mar. 14, 2006.
Turner et al., "Harnessing Asymmetrical Substrate Recognition by Thermostable Endov to Achieve Balanced Linear Amplification in Multiplexed Snp Typing", Biochemistry and Cell Biology, vol. No. 84, Issue No. 2, pp. 232-242, Apr. 2006.
Gao., "Biochemical Study of Endonuclease V and its Application in Mutation Scanning", Doctorate of Philosophy, Clemson University: pp. 1-176, May 7, 2007.
Gao et al., "Switching Base Preferences of Mismatch Cleavage in Endonuclease V: an Improved Method for Scanning Point Mutations", Nucleic Acids Research, vol. No. 35, Issue No. 01, pp. 1-6. Nov. 27, 2007.
Nakashima et al., "Amplifying Target Nucleic. Acid for Detection of Nucleic Acid, by Amplifying Nucleic Acid Using Oligonucleotide Primer Having Base Recognized by Endonuclease V, Endonuclease V and DNA Polymerase Having Chain Substitution Activity", Jan. 31, 2008.
PCT Search Report and Written Opinion issued in connection with Related Application No. PCT/US2008/050555 on Jul. 22, 2008.
US Non-Final Office Action issued in connection with Related U.S. Appl. No. 11/621,703 on Feb. 22, 2010.
US Non-Final Office Action issued in connection with Related U.S. Appl. No. 11/621,703 on Aug. 18, 2010.
Mi et al., "Dissecting Endonuclease and Exonuclease Activities in Endonuclease V from Thermotoga Maritima", Nucleic Acids Research, vol. No. 39, Issue No. 2, pp. 536-544, Sep. 17, 2010.
Huang et al., "Linear Nicking Endonuclease-Mediated Strand Displacement DNA Amplification", Analytical Biochemistry, vol. No. 414, pp. 58-69, 2011.
"Endonuclease V,T.maritima", Thermo Scientific, pp. 1-3, 2011.
US Non-Final Office Action issued in connection with Related U.S. Appl. No. 13/330,745 on Sep. 11, 2012.
US Final Office Action issued in connection with Related U.S. Appl. No. 13/330,745 on Mar. 25, 2013.
US Non-Final Office Action issued in connection with Related U.S. Appl. No. 13/330,745 on Aug. 5, 2013.
"Fluorescent Detection Reagent User Manual [online]", Mast Diagnostica.2005. Retrieved from internet; <URL:http://www.mast-diagnostica.com/MASTD_dt/PCR-Fly-67LMXXXX-Loopmap-Fluorescence-e.pdf>, p. 2, paragraph 1-2, retrieved on Feb. 13, 2014.
US Non-Final Office Action issued in connection with Related U.S. Appl. No. 13/330,745 on Aug. 6, 2014.
PCT Search Report and Written Opinion issued in connection with Related Application No. PCT/EP/2014/067321 on Nov. 12. 2014.
US Non-Final Office Action issued in connection with Related U.S. Appl. No. 13/965,696 on Jan. 2, 2015.

(56) References Cited

OTHER PUBLICATIONS

US Final Office Action issued in connection with Related U.S. Appl. No. 13/330,745 on Jan. 12, 2015.
European Search Report and Opinion issued in connection with corresponding EP Application No. 13809883.5 on Mar. 17, 2016.

\* cited by examiner

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 1
ccagcctggg catccttgan t                                              21

<210> SEQ ID NO 2

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Inosine
<220> FEATURE:
<221> NAME/KEY: misc_feature
<222> LOCATION: (21)..(22)
<223> OTHER INFORMATION: Phosphorothioate linkage

<400> SEQUENCE: 2
ttcagctctc ggaacatctc na                                             22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 3
tcacgcccac ggatctgaan g                                              21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Inosine
<220> FEATURE:
<221> NAME/KEY: misc_feature
<222> LOCATION: (21)..(22)
<223> OTHER INFORMATION: Phosphorothioate linkage

<400> SEQUENCE: 4
catccagtgg tttcttcttt ng                                             22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 5
```
gagaggagct ggtgttgttn g                                          21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 6
tgctcgctta gtgctccctn g                                          21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 7
ttgtgcctgt cctgggagan a                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 8
gacggaacag ctttgaggtn c                                          21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:

```
<221> NAME/KEY: misc_feature
<222> LOCATION: (20)..(21)
<223> OTHER INFORMATION: Phosphorothioate linkage

<400> SEQUENCE: 9
cacactggaa gactccagtn g                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Inosine
<220> FEATURE:
<221> NAME/KEY: misc_feature
<222> LOCATION: (19)..(20)
<223> OTHER INFORMATION: Phosphorothioate linkage

<400> SEQUENCE: 10
tgggcggcat gaaccggang                                                20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Inosine
<220> FEATURE:
<221> NAME/KEY: misc_feature
<222> LOCATION: (21)..(22)
<223> OTHER INFORMATION: Phosphorothioate linkage

<400> SEQUENCE: 11
ctacatgtgt aacagttcct nc                                             22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Inosine
<220> FEATURE:
<221> NAME/KEY: misc_feature
<222> LOCATION: (20)..(21)
<223> OTHER INFORMATION: Phosphorothioate linkage

<400> SEQUENCE: 12
cctgaggttg gctctgactn t                                              21

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (16)..(16)
<223> OTHER INFORMATION: Inosine
<220> FEATURE:
<221> NAME/KEY: misc_feature
<222> LOCATION: (16)..(17)
<223> OTHER INFORMATION: Phosphorothioate linkage

<400> SEQUENCE: 13
gcctcagcct cccgant                                                          17

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine
<220> FEATURE:
<221> NAME/KEY: misc_feature
<222> LOCATION: (17)..(18)
<223> OTHER INFORMATION: Phosphorothioate linkage

<400> SEQUENCE: 14
ctgggattac aggcatnc                                                         18

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Inosine
<220> FEATURE:
<221> NAME/KEY: misc_feature
<222> LOCATION: (16)..(17)
<223> OTHER INFORMATION: Phosphorothioate linkage

<400> SEQUENCE: 15
ctcccgggtt caagcna                                                          17

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine
<220> FEATURE:
<221> NAME/KEY: misc_feature
<222> LOCATION: (17)..(18)
<223> OTHER INFORMATION: Phosphorothioate linkage

<400> SEQUENCE: 16
gagatctcag ctcaccnc                                                         18

<210> SEQ ID NO 17
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine
<220> FEATURE:
<221> NAME/KEY: misc_feature
<222> LOCATION: (17)..(18)
<223> OTHER INFORMATION: Phosphorothioate linkage

<400> SEQUENCE: 17
caggctggag tgtaatng                                                       18

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Inosine
<220> FEATURE:
<221> NAME/KEY: misc_feature
<222> LOCATION: (18)..(19)
<223> OTHER INFORMATION: Phosphorothioate linkage

<400> SEQUENCE: 18
gacggagttt cactcttnt                                                      19

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine
<220> FEATURE:
<221> NAME/KEY: misc_feature
<222> LOCATION: (17)..(18)
<223> OTHER INFORMATION: Phosphorothioate linkage

<400> SEQUENCE: 19
ctgaggtcgg gagtttna                                                       18

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: Inosine
<220> FEATURE:
<221> NAME/KEY: misc_feature
<222> LOCATION: (16)..(17)
<223> OTHER INFORMATION: Phosphorothioate linkage

<400> SEQUENCE: 20
```
gaggccaagg cgagtnn                                                              17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Inosine
<220> FEATURE:
<221> NAME/KEY: misc_feature
<222> LOCATION: (16)..(17)
<223> OTHER INFORMATION: Phosphorothioate linkage

<400> SEQUENCE: 21
ggcgcagtgg ctcacna                                                              17

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine
<220> FEATURE:
<221> NAME/KEY: misc_feature
<222> LOCATION: (17)..(18)
<223> OTHER INFORMATION: Phosphorothioate linkage

<400> SEQUENCE: 22
aaaatggggt aaggggnc                                                             18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine
<220> FEATURE:
<221> NAME/KEY: misc_feature
<222> LOCATION: (17)..(18)
<223> OTHER INFORMATION: Phosphorothioate linkage

<400> SEQUENCE: 23
acccccgtca aactcant                                                             18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Inosine
<220> FEATURE:
<221> NAME/KEY: misc_feature -continued

```
<222> LOCATION: (18)..(19)
<223> OTHER INFORMATION: Phosphorothioate linkage

<400> SEQUENCE: 24
gtcatatact cagccctnc                                                  19

<210> SEQ ID NO 25
<211> LENGTH: 225
<212> TYPE: PRT
<213> ORGANISM: Escherichia coli

<400> SEQUENCE: 25
```

Met Ile Met Asp Leu Ala Ser Leu Arg Ala Gln Gln Ile Glu Leu Ala
1               5                  10                  15

Ser Ser Val Ile Arg Glu Asp Arg Leu Asp Lys Asp Pro Pro Asp Leu
            20                  25                  30

Ile Ala Gly Ala Asp Val Gly Phe Glu Gln Gly Gly Glu Val Thr Arg
        35                  40                  45

Ala Ala Met Val Leu Leu Lys Tyr Pro Ser Leu Glu Leu Val Glu Tyr
    50                  55                  60

Lys Val Ala Arg Ile Ala Thr Thr Met Pro Tyr Ile Pro Gly Phe Leu
65                  70                  75                  80

Ser Phe Arg Glu Tyr Pro Ala Leu Leu Ala Ala Trp Glu Met Leu Ser
                85                  90                  95

Gln Lys Pro Asp Leu Val Phe Val Asp Gly His Gly Ile Ser His Pro
            100                 105                 110

Arg Arg Leu Gly Val Ala Ser His Phe Gly Leu Leu Val Asp Val Pro
        115                 120                 125

Thr Ile Gly Val Ala Lys Lys Arg Leu Cys Gly Lys Phe Glu Pro Leu
    130                 135                 140

Ser Ser Glu Pro Gly Ala Leu Ala Pro Leu Met Asp Lys Gly Glu Gln
145                 150                 155                 160

Leu Ala Trp Val Trp Arg Ser Lys Ala Arg Cys Asn Pro Leu Phe Ile
                165                 170                 175

Ala Thr Gly His Arg Val Ser Val Asp Ser Ala Leu Ala Trp Val Gln
            180                 185                 190

Arg Cys Met Lys Gly Tyr Arg Leu Pro Glu Pro Thr Arg Trp Ala Asp
        195                 200                 205

Ala Val Ala Ser Glu Arg Pro Ala Phe Val Arg Tyr Thr Ala Asn Gln
    210                 215                 220

Pro
225

```
<210> SEQ ID NO 26
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26
```

Met Ile Met Asp Leu Ala Ser Leu Arg Ala Gln Gln Ile Glu Leu Ala
1               5                  10                  15

Ser Ser Val Ile Arg Glu Asp Arg Leu Asp Lys Asp Pro Pro Asp Leu
            20                  25                  30

Ile Ala Gly Ala Asp Val Gly Phe Glu Gln Gly Gly Glu Val Thr Arg
        35                  40                  45

Ala Ala Met Val Leu Leu Lys Tyr Pro Ser Leu Glu Leu Val Glu Tyr
        50                  55                  60

Lys Val Ala Arg Ile Ala Thr Thr Met Pro Ala Ile Pro Gly Phe Leu
 65                  70                  75                  80

Ser Phe Arg Glu Tyr Pro Ala Leu Leu Ala Ala Trp Glu Met Leu Ser
                85                  90                  95

Gln Lys Pro Asp Leu Val Phe Val Asp Gly His Gly Ile Ser His Pro
            100                 105                 110

Arg Arg Leu Gly Val Ala Ser His Phe Gly Leu Leu Val Asp Val Pro
        115                 120                 125

Thr Ile Gly Val Ala Lys Lys Arg Leu Cys Gly Lys Phe Glu Pro Leu
130                 135                 140

Ser Ser Glu Pro Gly Ala Leu Ala Pro Leu Met Asp Lys Gly Glu Gln
145                 150                 155                 160

Leu Ala Trp Val Trp Arg Ser Lys Ala Arg Cys Asn Pro Leu Phe Ile
                165                 170                 175

Ala Thr Gly His Arg Val Ser Val Asp Ser Ala Leu Ala Trp Val Gln
            180                 185                 190

Arg Cys Met Lys Gly Tyr Arg Leu Pro Glu Pro Thr Arg Trp Ala Asp
        195                 200                 205

Ala Val Ala Ser Glu Arg Pro Ala Phe Val Arg Tyr Thr Ala Asn Gln
    210                 215                 220

Pro Leu Glu
225

<210> SEQ ID NO 27
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Leu Gln Met Asn Leu Glu Glu Leu Arg Arg Ile Gln Glu Glu Met
 1               5                  10                  15

Ser Arg Ser Val Val Leu Glu Asp Leu Ile Pro Leu Glu Glu Leu Glu
                20                  25                  30

Tyr Val Val Gly Val Asp Gln Ala Phe Ile Ser Asp Glu Val Val Ser
            35                  40                  45

Cys Ala Val Lys Leu Thr Phe Pro Glu Leu Glu Val Val Asp Lys Ala
 50                  55                  60

Val Arg Val Glu Lys Val Thr Phe Pro Ala Ile Pro Thr Phe Leu Met
 65                  70                  75                  80

Phe Arg Glu Gly Glu Pro Ala Val Asn Ala Val Lys Gly Leu Val Asp
                85                  90                  95

Asp Arg Ala Ala Ile Met Val Asp Gly Ser Gly Ile Ala His Pro Arg
            100                 105                 110

Arg Cys Gly Leu Ala Thr Tyr Ile Ala Leu Lys Leu Arg Lys Pro Thr
        115                 120                 125

Val Gly Ile Thr Lys Lys Arg Leu Phe Gly Glu Met Val Glu Val Glu
    130                 135                 140

Asp Gly Leu Trp Arg Leu Leu Asp Gly Ser Glu Thr Ile Gly Tyr Ala
145                 150                 155                 160

Leu Lys Ser Cys Arg Arg Cys Lys Pro Ile Phe Ile Ser Pro Gly Ser

```
              165                 170                 175
Tyr Ile Ser Pro Asp Ser Ala Leu Glu Leu Thr Arg Lys Cys Leu Lys
            180                 185                 190

Gly Tyr Lys Leu Pro Glu Pro Ile Arg Ile Ala Asp Lys Leu Thr Lys
        195                 200                 205

Glu Val Lys Arg Glu Leu Thr Pro Thr Ser Lys Leu Lys
    210                 215                 220
```

METHOD FOR ISOTHERMAL DNA AMPLIFICATION STARTING FROM AN RNA TEMPLATE

SEQUENCE LISTING

The instant application contains a Sequence Listing which has been submitted electronically in ASCII format and is hereby incorporated by reference in its entirety. Said ASCII copy, created on Jan. 20, 2015, is named 248480-1_SL.txt and is 15,540 bytes in size.

FIELD OF THE INVENTION

The invention generally relates to methods for synthesizing a deoxyribonucleic acid (DNA) starting from a ribonucleic acid (RNA) template in a single reaction through the use of a reverse transcriptase, an endonuclease and a DNA polymerase to amplify the desired DNA, generally under isothermal conditions.

BACKGROUND

Nucleic acid amplification techniques are often employed in nucleic acid-based assays used for analyte detection, sensing, forensic and diagnostic applications, genome sequencing, whole-genome amplification, and the like. These applications often require nucleic acid amplification techniques having high specificity, sensitivity, accuracy, and robustness. The amplification of nucleic acids is particularly important when the starting nucleic acid material is present in small amounts.

Various techniques are currently used to amplify nucleic acids, some of which start with only a few molecules of nucleic acid material. These techniques include but are not limited to polymerase chain reaction (PCR), ligase chain reaction (LCR), self-sustained sequence replication (3SR), nucleic acid sequence based amplification (NASBA), strand displacement amplification (SDA), multiple displacement amplification (MDA) and rolling circle amplification (RCA). Several methods are currently available for reverse transcription of RNA to DNA, followed by amplification of the DNA. The current methods of reverse transcription of RNA to DNA and the subsequent amplification of the DNA involves two steps and under different conditions.

In polymerase chain reaction (PCR), a template DNA, a pair of primers, and a DNA polymerase are combined and subjected to repeat temperature cycling that permits melting, annealing, and elongation steps. The melting or denaturation step typically occurs at a high temperature, limiting the choice of polymerases to thermophilic polymerases and the step may further increase the equipment requirements. Alternative amplification methods using strand displacement DNA polymerase, inosine-containing primers, and Endonuclease V under isothermal conditions thereby eliminate the requirement for thermal cycling of the reaction to achieve nucleic acid amplification and the need for polymerase that is thermally stable; able to withstand repeated heating at high temperatures. The Endonuclease V, alternatively referred to as endo V or inosine 3' endonuclease, is a DNA repair enzyme that recognizes DNA containing nucleotides with deaminated or otherwise modified bases such as inosine. Endonuclease V cleaves the second (or third) phosphodiester bond 3' to the inosine in the same strand, leaving a nick with a 3'-hydroxyl and 5'-phosphate. In the amplification reaction, DNA polymerases add nucleotides to the 3' end of a pre-existing DNA strand resulting in 5'→3' elongation in a template-directed fashion to create a complementary strand. This extension reaction can include displacement of a pre-existing strand, resulting in a net increase in the number of copies of the DNA strand.

Amplification of an RNA template is required in, for example, RNA expression profiling. In this technique, the relative concentration of RNA molecules in a biological sample is determined. Some RNA molecules in a biological sample may be present in relatively low concentrations, such that there is a need to amplify the RNA prior to analysis in order to allow robust detection and analysis. Amplification of mRNA by PCR leads to RNA production of different molecular species at different rates and can provide ambiguous results, making RNA quantification difficult. In addition, the analysis requires at least three steps and different conditions. Currently available RNA amplification techniques suffer from high background noise, which may result from non-specific amplification reactions.

Better methods and compositions for amplification of DNA from an RNA template are desirable. Such methods and compositions should ideally be more robust, highly sensitive and reproducible.

BRIEF DESCRIPTION

One embodiment of a method comprises reverse-transcribing a ribonucleic acid (RNA) template to form a cDNA using a first reaction mixture comprising RNA template, at least one primer capable of hybridizing to the RNA template, a reverse transcriptase and deoxynucleoside triphosphates (dNTPs); and amplifying the cDNA to form an amplified product using a second reaction mixture comprising at least one strand displacement DNA polymerase, at least one inosine-containing primer and a nuclease that is capable of nicking DNA 3' to an inosine residue of the primer. The method is accomplished under an isothermal condition without denaturing the cDNA template.

Another embodiment of a method of quantifying a ribonucleic acid (RNA) template from a sample comprises reverse-transcribing the RNA to form a cDNA using a first reaction mixture comprising RNA template, at least one primer capable of hybridizing to the RNA template, a reverse transcriptase and deoxynucleoside triphosphates (dNTPs); and amplifying the cDNA to form an amplified product using a second reaction mixture comprising at least one strand displacement DNA polymerase, at least one inosine-containing primer and a nuclease that is capable of nicking DNA 3' to an inosine residue of the primer; analysing a rate of synthesis of the amplification product to quantify the RNA template present in the sample, wherein the reverse transcribing and amplifying are achieved under isothermal condition without denaturing the cDNA template.

In one embodiment, a method of quantifying a ribonucleic acid (RNA) template from a sample comprises reverse-transcribing the RNA to form a cDNA using a first reaction mixture comprising RNA template, at least one primer capable of hybridizing to the RNA template, a reverse transcriptase and deoxynucleoside triphosphates (dNTPs); and amplifying the cDNA to form an amplified product using a second reaction mixture comprising at least one strand displacement DNA polymerase, at least one inosine-containing primer and a nuclease that is capable of nicking DNA 3' to an inosine residue of the primer; and detecting a presence of the amplification product using a nucleic acid detection system. The reverse transcribing and amplifying are achieved under isothermal condition without denaturing the cDNA template.

In yet another embodiment, a method of amplifying a ribonucleic acid (RNA) template comprises reverse-transcribing the RNA template to cDNA; and amplifying the cDNA to form an amplified product without denaturing the cDNA, wherein the reverse transcription and amplification occurs under an isothermal condition and in a single reaction mixture comprising the RNA template, at least one primer for capable of hybridizing to RNA, a reverse transcriptase, a strand displacement DNA polymerase, deoxyribonucleoside triphosphates (dNTPs), and at least one inosine-containing primer and a nuclease that is capable of nicking DNA 3' to an inosine residue of the primer.

DRAWINGS

These and other features, aspects, and advantages of the present invention will become better understood when the following detailed description is read with reference to the accompanying drawings in which like characters represent like parts throughout the drawings, wherein.

Figure 4:
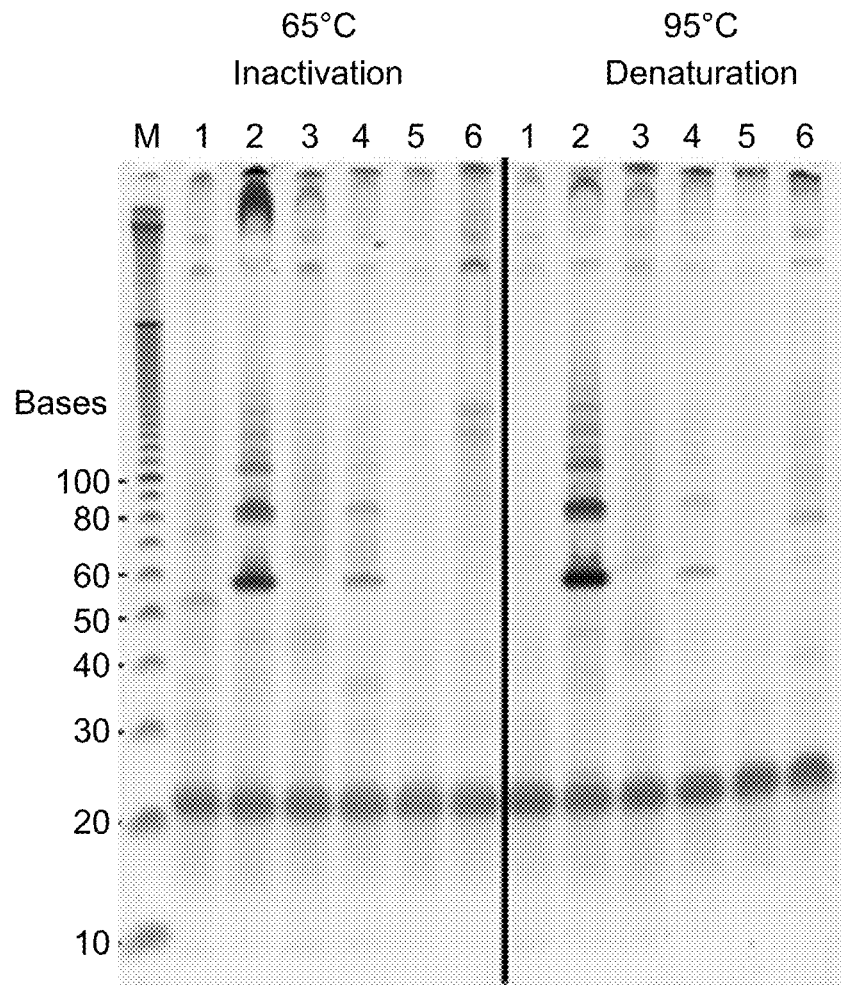

FIG. 4 provides an image of gel electrophoresis showing the DNA amplification product starting from an RNA or a cDNA template in the presence or the absence and of reverse transcriptase with or without denaturation of the template.

Figure 5:
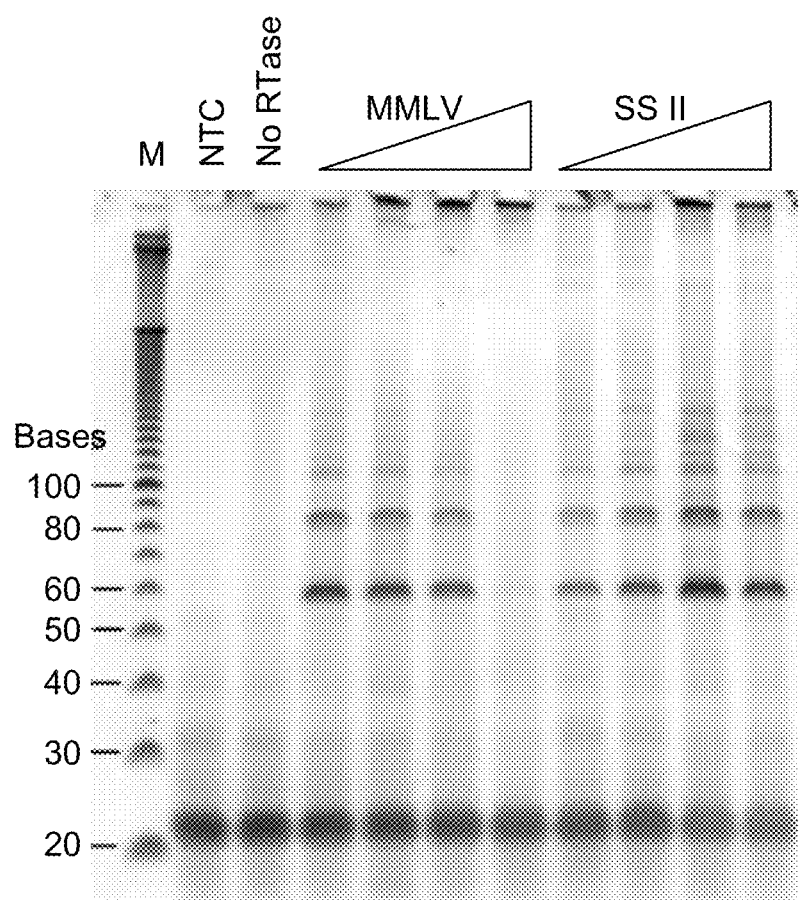

FIG. 5 provides an image of gel electrophoresis showing the DNA amplification product starting from an RNA template in the presence of increasing concentrations of two different reverse transcriptases.

Figure 6:
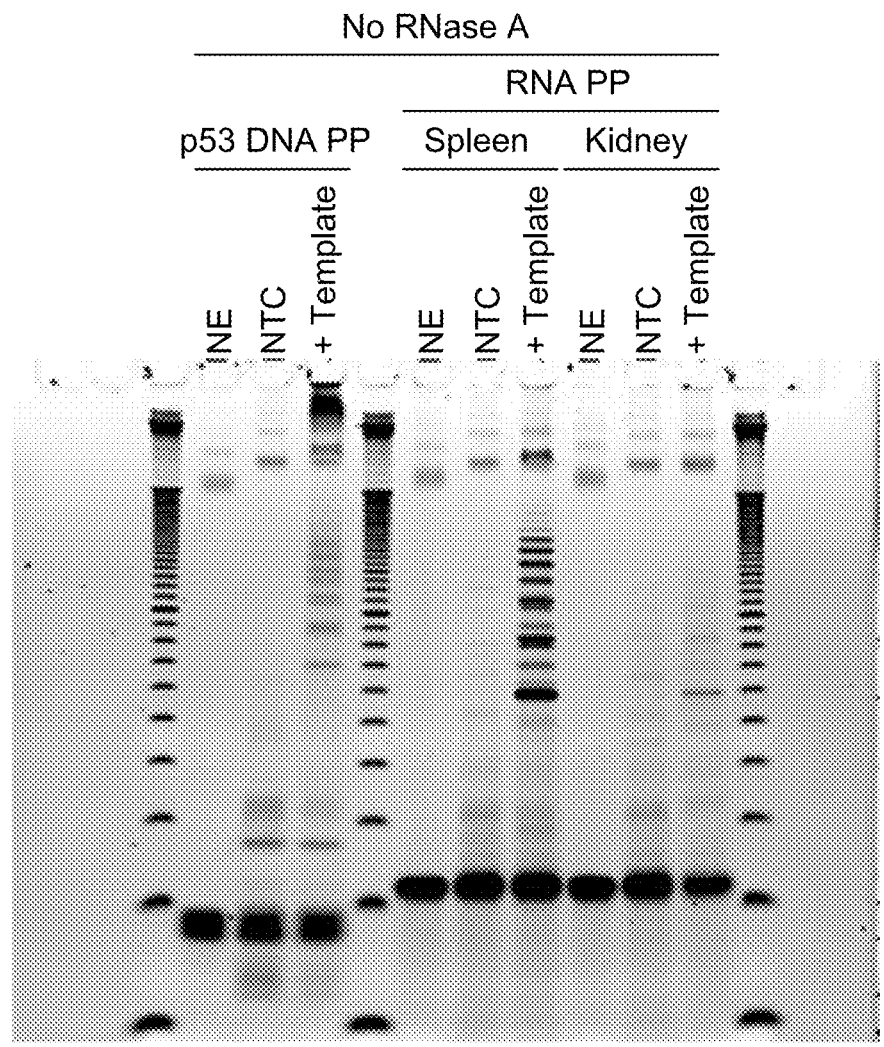

FIG. 6 is an image of gel electrophoresis showing the DNA amplification product of p53 sequence starting with either a DNA or an RNA template from spleen or kidney in the absence of RNase A.

Figure 7:
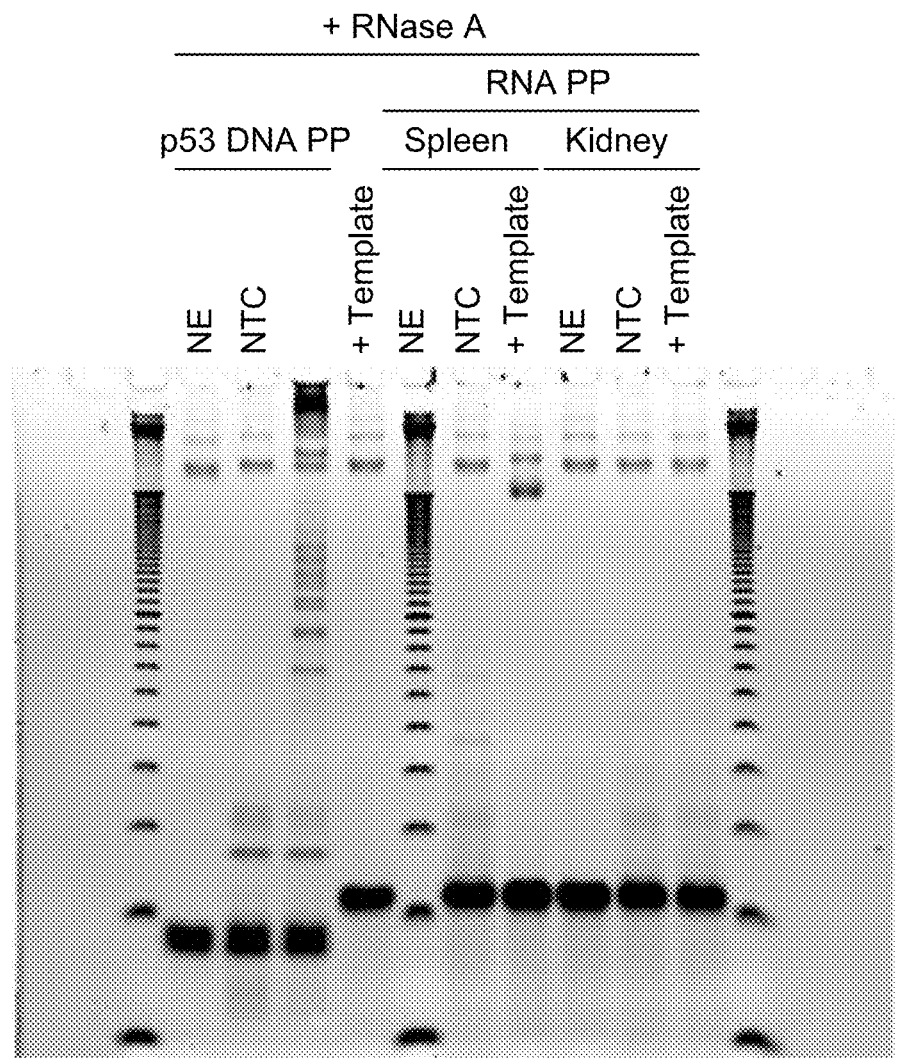

FIG. 7 provides an image of gel electrophoresis showing the DNA amplification product of p53 sequence starting with either a DNA or an RNA template from spleen or kidney that have been treated with RNase A as a negative control.

DETAILED DESCRIPTION

The invention is directed to methods and kits for DNA amplification from an RNA template. The methods generally comprise the steps of reverse transcription of the RNA template followed by amplification of the resultant DNA in a single reaction mixture. The present method allows production of adequate DNA for analyzing an RNA sample or gene expression starting from small number of cells or trace amounts of an RNA sample. The amplified cDNA, which is more easily quantified or interrogated, is produced from a small amount of RNA template. The methods utilize reverse transcriptase, DNA polymerase, endonuclease V and at least one primer containing an inosine (inosine-containing primer) nucleotide, and accomplish both the RNA reverse transcription and the DNA amplification without using a thermal cycling machine.

To more clearly and concisely describe and point out the subject matter of the claimed invention, the following definitions are provided for specific terms, which are used in the following description and the appended claims. Throughout the specification, use of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, "reverse transcriptase" generally refers to an enzyme capable of replicating RNA into a complementary DNA or cDNA. Reverse transcription is the process of copying an RNA template into DNA. In some embodiments, a reverse transcriptase is an enzyme capable of creating a DNA strand using an RNA strand as a template for synthesis. In one example, the enzyme optimally has the reverse transcriptase activity to generate a DNA from an RNA template, wherein the enzyme either does not have a DNA polymerase activity or has a minimal DNA polymerase activity. In another example, the enzyme has nominal DNA polymerase activity and high reverse transcriptase activity. Either a reverse transcriptase or a DNA polymerase with reverse transcriptase activity may generate a cDNA strand from RNA template. The reverse transcriptase may be a naturally occurring reverse transcriptase enzyme, or a variant or fragment thereof that retains the desired enzymatic activity described above. Any recombinantly engineered reverse transcriptase enzyme produced by routine methods in the field of molecular biology that has reverse transcriptase activity may be used in the practice of the present invention.

As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'→3' direction. Since DNA polymerase can only add a nucleotide onto a pre-existing 3'-OH group, to begin a DNA synthesis reaction the DNA polymerase needs a primer to which it can add the first nucleotide. Suitable primers comprise oligonucleotides of RNA or DNA. The DNA polymerase may be a naturally occurring DNA polymerases or a variant of natural enzyme having the above-mentioned activity. For example, it may include a DNA polymerase having a strand displacement activity, a DNA polymerase lacking 5'3' exonuclease activity, a DNA polymerase having a reverse transcriptase activity, or a DNA polymerase having an exonuclease activity.

As used herein, "a strand displacing nucleic acid polymerase" refers to a nucleic acid polymerase that has a strand displacement activity apart from its nucleic acid synthesis activity. That is, a strand displacing nucleic acid polymerase can continue nucleic acid synthesis on the basis of the sequence of a nucleic acid template strand (i.e., reading the template strand) while displacing a complementary strand that had been annealed to the template strand. Strand displacement is necessary to result in synthesis of multiple copies of a target sequences. A 5'→3' exonuclease activity, if present, might result in the degradation of a synthesized strand, and therefore, in some examples, the strand displacement DNA polymerases without a 5'→3' exonuclease activity are preferable. Any naturally occurring DNA polymerase, or a variant or fragment thereof that retains DNA polymerase activity, or any recombinantly engineered DNA polymerase that exhibits the desired enzymatic activity (e.g., DNA polymerase activity) may be used in the methods and kits disclosed herein. Methods for the production of a recombinant protein, particularly an enzyme, and more particularly a DNA polymerase, are well known and routine in the art of molecular biology.

As used herein, the term "Endonuclease V" or "endo V" or "inosine 3' endonuclease" refers to an enzyme has endonuclease activity. Typically the Endonuclease V is a DNA repair enzyme that recognizes DNA containing inosines and hydrolyzes the second or third phosphodiester bonds 3' to the inosine, leaving a nick with 3'-hydroxyl and 5'-phosphate. Endonuclease V is found organisms from *E. coli* to humans, and any Endonuclease V enzyme may be used in the reaction to provide nick formation at the DNA 3' relative to an inosine analog. The Endonuclease V may also recognize DNA containing xanthine or hypoxanthine and hydrolyzes the second or third phosphodiester bonds 3' to the xanthine or hypoxanthine residue, leaving a nick with 3'-hydroxyl and 5'-phosphate. The endonuclease used may be a naturally occurring nuclease, or a variant or fragment thereof that retains the enzymatic activity. Any engineered recombinant nuclease produced by standard methods in the field of molecular biology that exhibit the desired enzymatic activity (e.g., nuclease activity) may be used in the practice of the present invention. One of skill in the art would have the technical skill to produce a recombinant protein (e.g., an enzyme such as a reverse transcriptase, a DNA polymerase, or a nuclease) and would appreciate that such recombinant proteins can be made by a variety of molecular biology techniques.

As used herein, "primer", or "primer sequence" generally refers to a linear oligonucleotide that is complementary to and anneals to a target sequence. The lower limit on primer length is determined by ability to hybridize since very short primers (e.g., less than 5 nucleotides) do not form thermodynamically stable duplexes under most hybridization conditions. Primers typically vary in length from 8 to 50 nucleotides. In some embodiments, the primer is between about 15 and 25 nucleotides. The primers used herein include at least one inosine positioned near the 3' end of the primer (e.g., at the penultimate nucleotide of the 3' end of the primer). As used herein, the term "forward primer" refers to a primer that includes an inosine or inosine analog at the penultimate 3' position, which anneals to one particular strand of the target DNA. As used herein the term "reverse primer" refers to a primer that includes an inosine or inosine analog at the penultimate 3' position that anneals to the opposite strand of the target DNA. Together a forward primer and a reverse primer are generally oriented on the target DNA sequence in a manner analogous to PCR primers, such that their 3' ends are both closer to the target sequence than their 5' ends. Both naturally occurring nucleotides, specifically guanine, adenine, cytosine and thymine, hereinafter "G", "A", "C", and "T" and nucleotide analogs may be used for primers of the present method and composition.

As used herein the term "melting temperature" with respect to a primer refers to the temperature at which 50% of primer-DNA hybrids dissociate into free primer and DNA. The melting temperature of a primer increases with primer length. The melting temperature of a primer can also depend on its nucleotide composition. Thus, primers with multiple G and C nucleotides will melt at higher temperatures than ones that only have A and T nucleotides. High melting temperatures (e.g., above 65° C.) and very high melting temperatures (e.g., above 80° C.), may not be favorable in certain embodiments because some DNA polymerases denature and lose activity at such high temperatures. Because ionic strength also affects the melting temperature of a primer, all melting temperature values provided herein are determined at a pH of 7.7 with 5 mM $MgCl_2$ and 50 mM NaCl unless otherwise indicated.

As used herein, "amplification product" refers to amplified nucleic acids that are generated by nucleic acid amplification from a nucleic acid template.

As used herein, "template DNA" or "template RNA" refers to nucleic acids that are the desired target for amplification. For example, the template RNA is reverse transcribed to cDNA and the template cDNA is used to produce amplification product.

As used herein, the term "nucleotide analog" refers to compounds that are structurally similar to naturally occurring nucleotides. The nucleotide analog may have an altered phosphate backbone, sugar moiety, nucleobase, or combinations thereof. Generally, nucleotide analogs with altered nucleobases confer, among other things, different base pairing and base stacking proprieties. Nucleotide analogs having an altered phosphate-sugar backbone (e.g., Peptide Nucleic Acid (PNA) or Locked Nucleic Acid (LNA)) often modify, among other things, the chain properties such as secondary structure formation.

The term "amplicon" or "amplified product" generally refers to a DNA or RNA amplification product containing one or more target DNA or RNA sequences that result from the amplification of a target DNA driven by endonuclease nicking of an inosine-containing primer coupled with polymerase extension. Amplicons may be generated, for example, using a single inosine-containing primer, paired inosine-containing primers, or nested-paired inosine-containing primers. An amplicon may comprise single-stranded or double-stranded DNA, DNA:RNA hybrids, or RNA. Amplicons may comprise a mixture of amplification products (i.e., a mixed amplicon population), several dominant species of amplification products (i.e., multiple, discrete amplicons), or a single dominant species of amplification product (i.e., DNA or RNA). In some embodiments, a single species of amplicon may be isolated from a mixed population using techniques known in the art, such as affinity purification or electrophoresis. An amplicon may be largely single-stranded or partially or completely double-stranded DNA, DNA:RNA hybrids, or RNA depending on the reaction scheme used.

The term "conservative variants" as used herein applies to both amino acid and nucleic acid sequences. With respect to particular nucleic acid sequences, the term "conservative variants" refers to those nucleic acids that encode identical or similar amino acid sequences and include degenerate sequences. For example, the codons GCA, GCC, GCG, and GCU all encode the amino acid alanine. Thus, at every amino acid position where an alanine is specified, any of these codons may be used interchangeably in constructing a corresponding nucleotide sequence. Such nucleic acid variants are conservative variants, since they encode the same protein, assuming that is the only alternation in the sequence. One skilled in the art will recognize that each codon in a nucleic acid, except for AUG (i.e., the sole codon for the amino acid methionine) and UGG (i.e., the sole codon for the amino acid tryptophan), may be modified conservatively to yield a functionally identical peptide or protein. With regard to amino acid sequences, one skilled in the art will recognize that substitutions, deletions, or additions to a polypeptide or protein sequence which alter, add, or delete a single amino acid or a small number of amino acids (e.g., typically less than about ten amino acids) is a "conservative variant", wherein the alteration results in the substitution of one amino acid with a chemically similar amino acid.

The term "complementary," as used herein, refers to the capacity for precise pairing between nucleotides within an oligonucleotide or polynucleotide. For example, A pairs with T and G pairs with C by hydrogen bonding. If a nucleotide at a certain position of an oligonucleotide is capable of hydrogen bonding with a nucleotide at a corresponding position within a DNA molecule, then the oligonucleotide and the DNA are considered to be complementary to each other at that position. The whole oligonucleotide and the DNA are considered complementary to each other when a sufficient number of corresponding positions in each have nucleotides that hydrogen bond with each other.

As used herein, the term "dNTP mixture" generally refers to a combination of deoxynucleotides containing a phosphate, sugar, and organic base in the triphosphate form, that provide precursors required by a DNA polymerase for DNA synthesis. A dNTP mixture may include each of the naturally occurring deoxynucleotides (i.e., adenine (A), guanine (G), cytosine (C), uracil (U), and thymine (T)). In some embodiments, each of the naturally occurring deoxynucleotides may be replaced or supplemented with a synthetic analog; provided however that inosine may not replace or supplement G in a dNTP mixture.

As used herein, the term "inosine" refers to a 2'-deoxyribonucleoside or ribonucleoside having an analog of the normal bases, particularly the deaminated or similar bases recognized and cleaved by endonuclease V when encountered in DNA. As used herein the term "inosine analog" refers to a 2'-deoxyribonucleoside or ribonucleoside, wherein the base includes, for example, hypoxanthine (i.e., inosine proper), xanthine, uridine, oxanine (i.e., oxanosine), other O-1 purine analogs, N-6-hydroxylaminopurine, nebularine, 7-deaza hypoxanthine, other 7-deazapurines, and 2-methyl purines.

As used herein, the term "inosine-containing primer" refers to a primer including at least one inosine or inosine analog.

As used herein, the terms "reducing agent" or "reducing agents" refer to agents that reduce disulfides to mercaptans. Suitable reducing agents may contain thiol groups such as dithiothreitol (DTT), 2-mercaptoethanol (βME), and 2-mercaptoethylamine (MEA). Alternatively, reducing agents may contain phosphines and their derivatives, for example, Tris (carboxyethyl)phosphine (TCEP).

As used herein the term "single strand DNA binding protein", abbreviated as "SSB", refers to proteins that non-covalently bind to single stranded DNA with a higher affinity than that to a double stranded DNA. Suitable examples of single strand binding proteins include, but are not limited to, E. coli SSB, T4 gene 32 protein, T7 gene 2.5 protein, Ncp7, recA, or combinations thereof.

As used herein, the term "target DNA" refers to a DNA sequence region of natural or synthetic origin that may be synthesized or amplified using one of more of the methods or compositions of the present invention.

As used herein, the term "template" refers to the portion of the target RNA or DNA that is amplified by a DNA polymerase to produce one or more amplification products or amplicons.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

In one example, the method comprises reverse-transcribing an RNA template to form a cDNA, and then amplifying the cDNA to form an amplification product. The reverse transcription is achieved using a first reaction mixture comprising an RNA template, at least one primer capable of hybridizing to the RNA, a reverse transcriptase, and deoxynucleoside triphosphates (e.g. dNTPs) to produce cDNA. As noted, the method further comprises amplification of the cDNA to form an amplification product using a second reaction mixture comprising at least one strand displacement DNA polymerase, at least one inosine-containing primer, and a nuclease (e.g., Endo V) that is capable of nicking DNA 3' to an inosine residue of the primer. The entire method beginning with an RNA template and resulting in the production of cDNA amplification product, which is accomplished under an isothermal condition without denaturing the cDNA.

In one embodiment, the reverse transcription and amplification steps are performed in a single reaction mixture. The method for amplification of an RNA template comprises reverse-transcribing the RNA template to a cDNA followed by amplifying the cDNA to generate a DNA amplification product, wherein the amplification proceeds without denaturing the cDNA. In some embodiments, the reverse transcription and amplification processes occur under isothermal conditions in a single reaction mixture. In one or more aspects of the methods, the single reaction mixture refers to a composition that comprises all of the necessary reagents for the reverse transcription step (i.e., step one) and the DNA amplification (i.e., step two). The single reaction mixture above may comprise an RNA template, a reverse transcriptase, one or more primers capable of hybridizing to the RNA template, a DNA polymerase, one or more primers containing a modified base capable of hybridizing to cDNA (e.g., inosine-containing primers), dNTP's, and an endonuclease that is capable of nicking DNA 3' to an inosine residue of the primer.

In some embodiments of the methods, the reverse transcription and amplification reactions may occur either consecutively in two separate steps or simultaneously. In one aspect, the RNA template reverse-transcribed to cDNA, and the amplification step then proceeds with the cDNA serving as the template. In one embodiment, the amplification step occurs after the reverse transcription step. In some other embodiments, when the method is performed simultaneously, the reverse transcription of the RNA template and amplification of the cDNA proceeds, at the same time. In one or more embodiments, when the amplification starts from the RNA template and occurs in a single reaction mixture under isothermal conditions, the single reaction mixture comprises all of the reagents necessary for reverse transcription and DNA amplification.

Figure 3:
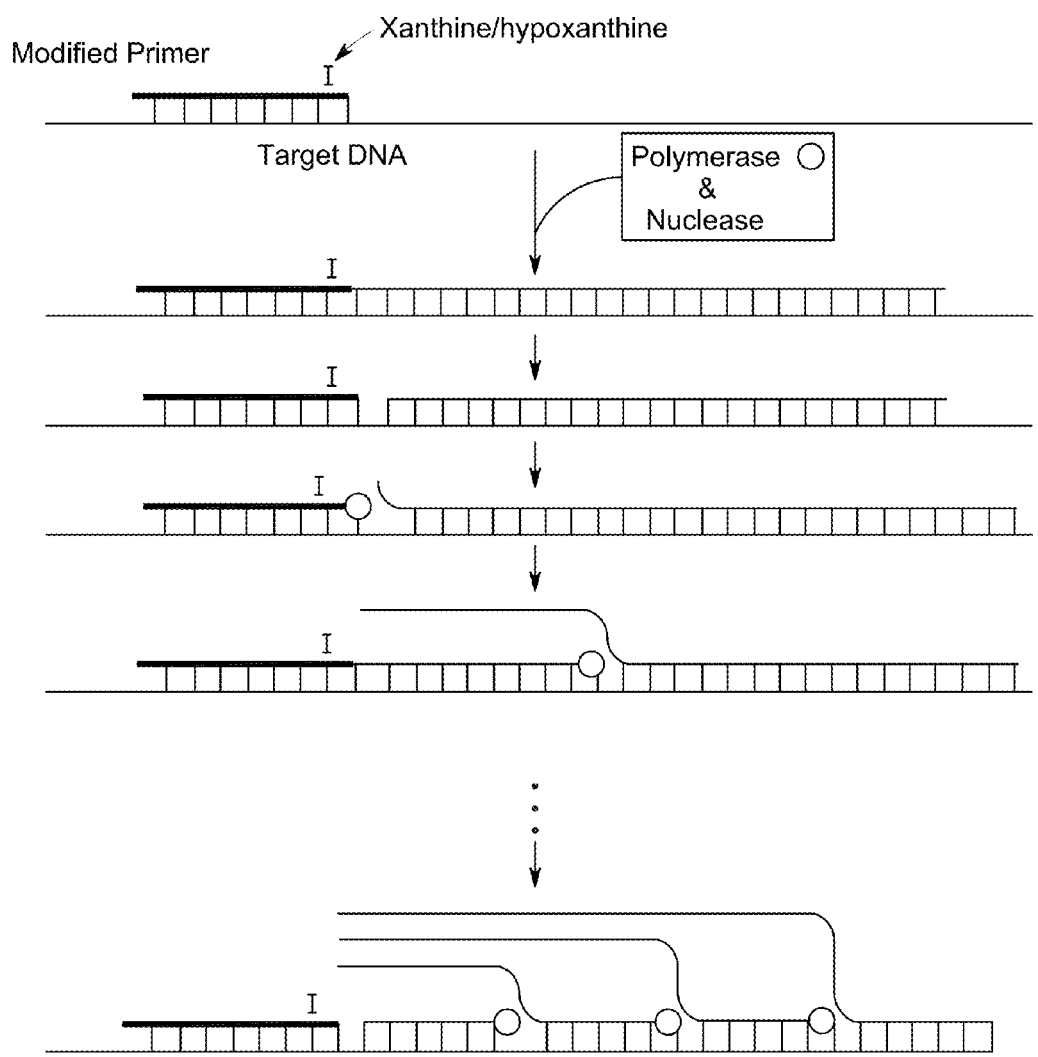
FIG. 3 is a schematic presentation of a DNA amplification mechanism using primers with modified bases and strand displacement DNA polymerase.

In certain aspects, the reverse transcription step generates single stranded cDNA, a double stranded cDNA, an RNA:cDNA heteroduplex or a combination thereof. The use of an inosine-containing primer in an amplification reaction is advantageous, as the inosine-containing primer can bind to any form of the template cDNA, such as a single stranded, a double stranded or a heteroduplex cDNA, and can initiate amplification of the template cDNA. The inosine-containing primer forms a primer: template hybrid, wherein a nuclease forms a nick at the 3' DNA of the primer, next to the inosine residue. The strand displacing DNA polymerase binds to the nicked strand and initiates synthesizing complementary DNA strand. One or more exemplary embodiments are shown in FIG. 3, which is described in further detail below.

As noted above, the method comprises reverse-transcribing an RNA template to a cDNA template, wherein the reverse transcription requires a reverse transcriptase. Exemplary embodiments of reverse transcriptase include, but are not limited to reverse transcriptase from human immunodeficiency virus (HIV) type 1, reverse transcriptase from moloney murine leukemia virus (MMLV RT), and reverse transcriptase from avian myeloblastosis virus (AMV RT). Some of the reverse transcriptase enzymes have increased heat stability, for example, the SuperScript™ II or SSII™ reverse transcriptase, which synthesizes cDNA at about 42° C. In some embodiments, the reverse transcriptase (e.g., SS II™) binds to a single stranded RNA, a single stranded DNA or a DNA-RNA hybrid. The reverse transcriptase provides specificity and higher yields of full-length product.

In one or more embodiments, some of the reverse transcriptase enzymes may have Ribonuclease H(RNase H) activity (e.g., MMLV RT). The enzymes with RNase H activity tend to degrade the RNA template, specifically hydrolyzing the phosphodiester bonds of RNA in an RNA:DNA hybrid and produce 3'-OH and 5'-P-terminated products. A single-stranded nucleic acid, a double-stranded DNA, or a double-stranded RNA is resistant to RNase H activity. In certain aspects, the reverse transcriptase is mutated to reduce the RNase H activity, such as SSII™ reverse transcriptase (Invitrogen™). The SSII™ reverse transcriptase is a mutated form of MMLV reverse transcriptase, wherein the MMLV reverse transcriptase is mutated to reduce the RNase H activity. The advantage of a reverse transcriptase having reduced RNase H activity is that it provides better stability of the template RNA. In some embodiments, where the reverse transcriptase has more RNase H activity, the enzyme degrades the template RNA.

In some embodiments, one or more of the DNA polymerases in the reaction mixture has same degree of reverse transcriptase activity. In these embodiments, the DNA polymerase functions as a reverse transcriptase, when the polymerase has substantial activity for reverse transcription. An example of a DNA polymerase that possesses reverse transcriptase activity is Bst DNA polymerase. The Bst DNA polymerase, however, is not an efficient reverse transcriptase. For example, FIG. 4, lanes 5 at 65° C. and 95° C., which show no amplification product from a reaction mixture comprising RNA and Bst DNA polymerase, which thereby clearly supporting the observation that the Bst DNA polymerase is not an efficient reverse transcriptase. FIG. 4 shows an image of a gel, wherein the label "inactivation" or "denaturation" refers to a heating step, at a temperature of approximately 65° C. or 95° C., of the mixture of template RNA or template cDNA and primers prior to the addition of the enzyme mixture comprising reverse transcriptase, DNA polymerase and Endonuclease V.

The primer, which hybridizes to RNA template, is interchangeably used herein as "RNA primer". Similarly, the primer, which hybridizes to DNA template, is interchangeably used herein as "DNA primer". In some embodiments, the reverse transcription of an RNA template or amplification of a cDNA template may initiate using either of the DNA primer or the RNA primer. In some embodiments, the RNA primer comprises an inosine-containing primer, an oligonucleotide dT primer, a Locked Nucleic Acid (LNA), a Peptide Nucleic Acid (PNA) or a combination thereof. In some aspects of the methods, the primer employed for reverse transcription may comprise about eight to about twenty-five nucleotides. In one embodiment, the RNA primer comprises twenty nucleotides. In some other embodiments, the RNA primer may be complementary to the poly A tail of the RNA, wherein the primer may anneal to the poly A tail. As noted poly A tail of RNA, which refers to herein an RNA comprises multiple adenosine monophosphates and are situated at the tail (or end) of the RNA. In some other embodiments, the primer may be designed to be complementary to a specific sequence of the RNA template. In alternative embodiments, the RNA primer is a random primer designed to bind to a random sequence of the RNA template. The annealing temperature of the primer to the template RNA is selected to be in a range in which the reverse transcription reaction leads to the production of cDNA. In one or more aspects, an oligonucleotide primer comprising inosine is used for reverse transcription. In alternate embodiments, the RNA primers may also comprise xanthine in place of inosine.

The reverse transcription is typically performed under isothermal conditions, at a temperature in a range between 20° C. to 70° C. In some embodiments, the reverse transcription occurs at room temperature, (e.g., approximately at 30° C.). In one embodiment, the reverse transcription occurs at a temperature of, for example, about 45° C. The selection of the temperature for reverse transcription may depend on the functionality of various enzymes, such as the reverse transcriptase. In one embodiment, the reverse transcription employs SSII™ reverse transcriptase, which synthesizes cDNA from an RNA template at approximately 42° C. In additional embodiments, as the reverse transcription of the RNA template and cDNA amplification occur in a single reaction mixture, the optimum temperature of the reaction is selected such that the efficiency of DNA polymerase or the endonuclease may be deemed considerably high. Since some DNA polymerases and endonucleases have considerably higher efficiency at about 35-50° C., the optimum temperature for performance of both the reverse transcription and the DNA polymerization reactions may be selected to be about 45° C.

The reaction for DNA polymerization initiates with template cDNA and the reagents for DNA amplification reaction. In some embodiments, the reaction mixture comprises a DNA polymerase, dNTP's, inosine-containing primers and an endonuclease, and the reactions typically are performed at the same temperature (e.g., isothermal conditions).

In some embodiments, the reverse transcription reaction step occurs simultaneously with the DNA amplification reaction in a single reaction mixture. In an alternate embodiment, the reverse transcription reaction step occurs to produce cDNA, and the amplification reaction mixture is added separately to the cDNA at the same temperature condition to produce amplification products. In some examples of investigating multiple RNA species in a homogenous sample, the method of amplifying DNA from an RNA template under isothermal conditions may be appropriate as the multiple RNA species could be identified using one or more different detection methods. In some embodiments, the reverse transcription reaction step occurs to produce cDNA, and the amplification reaction mixture is added separately to the cDNA for amplification, wherein the reverse transcription and amplification occurs at two different temperature conditions. In some examples of investigating multiple RNA species in a sample, the method may be appropriate as the multiple RNA species are converted into cDNA in a combined reaction, and then the cDNA product is divided into separate amplification reactions to form DNA amplification products, wherein the reverse transcription and amplification occurs at two different temperature conditions. This example determines the presence of different RNA species in the initial sample.

An exemplary method of DNA amplification comprises annealing an inosine-containing primer to the template DNA to form a primer: template DNA hybrid. The amplification reaction further comprises the use of a nuclease to nick the primer: template DNA hybrid at the DNA 3' to an inosine residue of the primer. The nuclease functions in the presence of the DNA polymerase and dNTPs, wherein the DNA polymerase binds to the nicked DNA template, displaces the DNA strand and synthesizes another DNA strand with the dNTPs in the reaction mixture to produce at least one amplification product complementary to portions of the template DNA (or cDNA).

The methods for DNA amplification from an RNA template may involve the introduction of an inosine into a specific position of a template DNA using, for example, an oligonucleotide primer comprising an inosine. A DNA polymerase synthesizes DNA from a primer: DNA template hybrid, starting from the DNA 3' to the inosine residue. An endonuclease V then forms a nick to the DNA 3' of the inosine residue, allowing the DNA polymerase to bind to the nicked DNA template. The DNA polymerase then synthesizes a DNA strand, complementary to the template DNA, with simultaneous strand displacement. The repeated nick formation at the 3' DNA of the inosine residue by endonuclease V allows the DNA polymerase to bind to the nicked template in repeatedly to make the complementary strand to the target DNA, in a repetitive manner. In some other embodiments, the oligonucleotide primer comprises xanthine rather than inosine. In these embodiments, the endonuclease V forms a nick to the DNA 3' of the xanthine or hypoxanthine residue, thereby allowing the DNA polymerase to bind to the nicked DNA template.

In one or more embodiments, the primers for amplification reaction are selected from primers containing a modified nucleotide (e.g., a nucleotide analog). In some embodiments, a primer comprising inosine, or xanthine residue at different positions is used for the DNA amplification. In one embodiment, the inosine, or xanthine residue may be positioned at least 4 nucleotides, at least 5 nucleotides, or at least 10 nucleotides from the 5' end of the primer. In these embodiments, the inosine substitutes for a guanosine and is opposite to a cytosine or thymine base, but since inosine is considered to be "universal base" it could be place opposite to any base. In certain embodiments, the inosine nucleotide may be the penultimate 3' nucleotide of the primer. In other embodiments, the inosine may be the ultimate 3' nucleotide of the primer. In alternate embodiments, an inosine may be present at both the penultimate 3' and ultimate 3' positions of the primer, and since the nuclease nicks 2 nucleotides from the inosine, both inosines may be retained in the primer sequence during the amplification reaction.

In one or more embodiments, the first, second, or both reaction mixtures comprise multiple forward and reverse inosine-containing primers for annealing with the cDNA. In some embodiments, the inosine-containing primers may be synthesized using art-recognized synthesis techniques. Primer design software may be employed to design a single primer or multiple primers capable of annealing to a nucleic acid, thereby facilitating polymerase-mediated extension. The embodiments in which the reaction proceeds at a temperature in the range of 10° C.-50° C., the melting temperature of the primer is generally about 45° C. in approximately 50 mM salt. In other aspects of the instant application, relatively short primers (e.g., 10-mers to 20-mers; more particularly 14-mers to 18-mers, or 16-mers) may be employed. In other embodiments, the inosine-containing primer is about 5 to 100, 5 to 30, or 5 to 20 nucleotides in length.

In certain embodiments, an inosine-containing primer is designed such that the inosine residue is positioned in the primer at a location complementary to a C or T in the target DNA. In some embodiments, the inosine is positioned as the penultimate 3' base of the primer. Because reaction conditions such as temperature and ionic strength affect the efficiency of annealing of the primer to the target DNA, the position of the inosine in the primer may be adjusted according to the specific reaction conditions. In general, the inosine residue is positioned away from the 5' end of the primer so that the primer remains annealed to the target DNA after it is nicked by the endonuclease. Accordingly, the segment of the primer 5' of the inosine generally has a melting temperature approximately equal to the temperature of the chosen reaction conditions. If there are two template G's in a row, two inosines may appear in the primer as both the penultimate 3' and the ultimate 3' residues. The GG, AA, GA, AG and the combination of two or more of them also function well in a similar manner.

Multiple primers may be included in some reaction mixtures. Embodiments in which both the plus and minus DNA strands are generated, paired primers comprising a forward primer and a reverse primer may be included in the reaction mixture. The inclusion of multiple paired primers may improve the relative percentage of a discrete nucleic acid product in the reaction mixture. Nested primers may be designed to bind at or near the 3' end of the previous amplicon so that in a series, each primer in the series hybridizes next to or near each other on the original target nucleic acids. Embodiments in which multiple nested primers are used, a single strand binding protein (SSB), usually at a concentration of about 1 ng to 1 µg in a 10 µL volume, may be included in the reaction mixture to increase fidelity and reduce background. The SSB can be selected from any of the different SSB's known in the art, and chosen optimally based on compatibility with reagent conditions and cooperative interaction with the other enzymes used in reaction mixture.

One or more embodiments of the methods employ DNA polymerases that may demonstrate one or more of the following characteristics: strand displacement activity; the ability to initiate strand displacement from a nick; and low degradation activity for single stranded DNA. As noted, the DNA polymerization involves synthesis of DNA using DNA polymerase and nucleotide triphosphates. The DNA polymerase uses nucleotide triphosphates to add nucleotides to the 3' end of a primer based on a template strand of DNA in a complementary fashion, creating a new DNA strand that is complementary to the original template DNA. In one or more embodiments, the amplified product may be a single stranded or double-stranded DNA, often extending to the end of the template strand.

Typically, the DNA polymerases having 3'→5' exonuclease activity allows the enzyme to proofread synthesized DNA by excision repair of the mismatched nucleotides in 3'→5' direction. In some embodiments, unlike DNA polymerases with 3'→5' exonuclease activity, the amplification employs exonuclease deficient DNA polymerase. The exonuclease deficient DNA polymerase is used to maintain repeated nicking at inosine 3' DNA in the absence of proofreading and it prevents the excision of inosine, allowing the use of the modified base. In some embodiments, the primers can be modified with thioated bases to prevent degradation by exonuclease activity. In one or more embodiments, the inosine-containing primer comprises a phosphorothioate linkage. A phosphorothioate linkage can be used to prevent 3'→5' exonuclease or endonuclease removal of inosine from the primer during amplification. The presence of phosphorothioate linkage is desired if the DNA polymerase used in the methods and kits of the instant invention has a proofreading 3'→5' exonuclease activity. This would also be advantageous if any of the enzymes used in the method possesses nuclease activity, or if the template used is contaminated with a nuclease. The nuclease resistant linkage may be located at any position within the primer, however in certain embodiments, the phosphorothioated linkages directly are attached to the 5' or 3' to the inosine.

In some embodiments, the exonuclease deficient DNA polymerase has a strand displacement activity. As the DNA polymerase binds to a nick formed by the endonuclease and synthesizes DNA from 3'→5' direction, the strand displacement activity is required for moving forward the DNA polymerase and synthesizing the complementary strand. In one or more embodiments, exemplary DNA polymerases useful for the methods include, but are not limited to, a Bst DNA polymerase, an exonuclease-deficient T7 DNA polymerase, an exo (−) Klenow, a delta Tts DNA polymerase, a BCA DNA polymerase, a Phi 29 DNA polymerase, a Sequenase 2, a T4 DNA polymerase, a T5 DNA polymerase and any combinations thereof.

As noted, in some embodiments, the method comprises an endonuclease, which forms a nick at the 3' end of the inosine or xanthine residue present in the primer. In one or more embodiments, the endonuclease is an Endonuclease V. In one embodiment, the Endonuclease V is a nuclease that specifically nicks DNA at two nucleotides 3' of an inosine nucleotide. The nick occurs on the same strand as the inosine when the target DNA is double stranded. The endonuclease, in combination with a strand displacing DNA polymerase and a primer produces targeted DNA amplification. First, the DNA polymerase extends the primer, creating a nicking site for the nuclease. Nicking creates an initiation site for the DNA polymerase, displacing a single-stranded DNA product while it re-creates the double-stranded primer extension product. The cycle repeats, synthesizing multiple single strands of DNA complementary to the downstream portion of the template.

Endonuclease V which is used herein recognizes DNA containing inosines and hydrolyzes the second or third phosphodiester bonds 3' to the inosine, leaving a nick with 3'-hydroxyl and 5'-phosphate. Any Endonuclease V enzyme nicks DNA 3' relative to an inosine analog. In some embodiments, wild type endonuclease V (e.g., SEQ ID NO: 25) may be employed in the inventive methods. In alternative embodiments, the variants provided herein as SEQ ID NO: 26 or SEQ ID NO: 27 may be used to nick the inosine-containing target DNA. In one or more embodiments, the Endonuclease V also recognizes DNA containing xanthine or hypoxanthine and hydrolyzes the second or third phosphodiester bonds 3' to the xanthine or hypoxanthine residue, leaving a nick with 3'-hydroxyl and 5'-phosphate. In embodiments where the target nucleic acid is not heat denatured, the endonuclease V variants which are employed herein have maximum activity at a relatively low temperature e.g., below 85° C., or between 20° C. and 80° C.

With a single, forward primer, the rate of synthesis of complementary copies of each molecule is relatively constant, resulting in a steady, linear increase in the number of copies with time. When second primer in the reverse direction is added, anneals to the template DNA at a defined distance from the forward primer, amplification process is accelerated. The forward and reverse primers may be placed relatively close to each other (i.e., less than about 1 kb apart), minimizing the time required to copy the forward amplicon to its 5' end as defined by the endonuclease V cleavage site, thereby increasing the kinetics and reducing the total time required to generate amplicons from the template DNA. The reaction rate reaches a maximum when the amount of nuclease or polymerase of other component becomes limiting. Additional nested primers may also be used to further increase amplification rates. In some embodiments, as the nicking reaction eliminates the replication of the primer sequences into the amplification products, one or more nested primers are required to further amplify the amplification products.

Reaction temperatures for amplification may vary during the amplicon production process ranging from 20° C. to 70° C. In some embodiments, the reaction temperature may be held at 40-50° C. In one embodiment, the reaction temperature may be held at 45° C.

In alternative embodiments, the method employ at least one extender template for amplification. The extender template is specific sequence, such as, a promoter sequence or a restriction endonuclease site specific sequence. An extender template may be designed so that the 3' end of the amplicon anneals to it. If the extender template contains two stretches of sequence, one complementary to the amplicon, and one that is not, and hybridization creates a 5' overhang of the non-complementary primer sequence, the 3' recessed end of the amplicon will be further extended by the DNA polymerase. This extension reaction may be employed to incorporate specific DNA sequences at the 3' end of the innermost amplicon. This extension reaction can also be used to displace a sequence from the 5' overhang.

In one or more embodiments, the 5' end of the extender template may contain a hairpin loop, with a fluorescent dye and a quencher located on either arm of the stem, then the dye fluorescence may be largely quenched by energy transfer. Upon extension by the strand displacing DNA polymerase from the recessed 3' end of the amplicon, the stem-loop structure becomes double stranded and the dye and quencher become further separated, eliminating some or all of the quenching, and generating a detectable signal. This signal may be multiplexed by the sequence of the extender template and the color of the quenched dye so that 2 or more independent amplification processes may be monitored simultaneously.

In some embodiments, the 5' end of the extender template may include the complement of an RNA polymerase promoter sequence. Thus, a double stranded RNA polymerase promoter may be generated by hybridization of extender template to the amplicon followed by extension by the DNA polymerase of the 3' end of the amplicon into the promoter region. In embodiments where an RNA polymerase is included in the reaction, the amplicon may be transcribed as a single-stranded RNA polymerase template. In all embodiments, the nucleic acids produced by the present methods may be determined qualitatively or quantitatively.

In some embodiments, the method of amplification of DNA from an RNA template further comprises analyzing a rate of synthesis of the amplification product to quantify the RNA template present in the sample. In some alternate embodiments, the method further comprises detecting the amplification product using a nucleic acid detection system. In some embodiments, the nucleic acid detection system comprises gel electrophoresis, an intercalating dye, a fluorescent label, an enzyme-linked label, an antibody-mediated label, and a radioactive label, or pyrophosphate quantitation.

DNA amplification product (amplified sequences) may be detected using any of the conventional detection systems for nucleic acids, such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired.

To aid in detection and quantitation of amplified nucleic acids, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use are radioactive isotopes, fluorescent molecules, phosphorescent molecules, enzymes, antibodies, and ligands.

Examples of suitable fluorescent labels include fluorescein (5-carboxyfluorescein-N-hydroxysuccinimide ester), rhodamine (5,6-tetramethyl rhodamine), fluorescein isothiocyanate (FITC), 5,6-carboxymethyl fluorescein, Texas red, nitrobenz-2-oxa-1,3-diazol-4-yl (NBD), coumarin, dansyl chloride, 4'-6-diamidino-2-phenylinodole (DAPI), and the cyanine dyes Cy3, Cy3.5, Cy5, Cy5.5 and Cy7.

Labeled nucleotides are another form of detection label since they can be directly incorporated into the amplification products during synthesis. Examples of detection labels that can be incorporated into amplified DNA or RNA include nucleotide analogs such as BrdUrd (BUDR triphosphate, Sigma), BrUTP and nucleotides modified with biotin or with suitable haptens such as digoxygenin. Suitable fluorescence-labeled nucleotides are Fluorescein-isothiocyanate-dUTP, Cyanine-3-dUTP and Cyanine-5-dUTP. BrdUrd is commonly used for a nucleotide analog detection label for DNA, Biotin-16-uridine-5'-triphosphate (Biotin-16-dUTP, Boehringer Mannheim) is commonly used for nucleotide analog detection for RNA. Fluorescein, Cy3, and Cy5 can be linked to dUTP for direct labelling. Cy3.5 and Cy7 are available as avidin or anti-digoxygenin conjugates for secondary detection of biotin or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,dioxetane-3-2'-(5'-chloro)tricyclo[3.3.1.1.sup.3,7]decane]-4-yl)phenyl phosphate; Tropix, Inc.). A detection label for use in detection of amplified RNA is acridinium-ester-labeled DNA probe. An acridinium-ester-labeled detection probe permits the detection of amplified RNA without washing because unhybridized probe can be destroyed with alkali.

Detection probes are labeled oligonucleotides having sequence complementary to detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Biotin and fluorescent molecules may be used for analyzing or quantifying an amplification product. Molecular beacons are detection probes labeled with fluorescent moieties where the fluorescent moieties fluoresce only when the detection probe is hybridized. The use of such probes eliminates the need for removal of unhybridized probes prior to label detection because the unhybridized detection probes will not produce a signal, which is especially useful in multiplex assays.

An address probe may also be used for quantitation of amplified product. The address probe is an oligonucleotide having a sequence complementary to address tags on primers. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

Molecules that combine two or more of these detection labels are also considered as detection labels. Any of the known detection labels can be used with the disclosed probes or tags, and detect amplified nucleic acid using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

In embodiments where terminal-phosphate-labeled ribonucleotides are used, the phosphatase may be used for color generation in a qualitative or quantitative assay. In such embodiments, the terminal phosphate may be protected from dephosphorylation by using terminal-phosphate methyl esters of dNTP's or deoxynucleoside tetraphosphates.

In one or more embodiments, the RNA template is isolated from eukaryotic origin, prokaryotic origin, viral origin, bacteriophage origin, or synthetic origin. In one or more embodiments, the samples suspected or known to contain a particular nucleic acid sequence, e.g., RNA, may be obtained from a variety of sources. The sample may be, for example, a biological sample, a food, an agricultural sample, or an environmental sample. In some embodiments, the samples are derived from a variety of biological subjects. The biological subject may comprise a prokaryotic or a eukaryotic origin. In some embodiments, the biological subject comprises a virus. In one or more embodiments, the nucleic acid samples derived from a biological subject may be derived from a biological tissue, whole cells, cell fractions, cell cultures or body fluid or exudate (e.g., blood, plasma, serum or urine, milk, cerebrospinal fluid, pleural fluid, lymph, tears, sputum, saliva, stool, lung aspirates, throat or genital swabs, and the like).

In one or more embodiments, the nucleic acid to be amplified (or target nucleic acid) is present in a sample, wherein the sample may be dispersed in a solution or may be immobilized on a solid support (such as blots, arrays, microtiter, or well plates). In some embodiments, the sample may be pretreated to make the target nucleic acid available for hybridization. In some embodiments, when the target nucleic acid is present in a double stranded form, the double stranded nucleic acid is amplified without denaturing the nucleic acid. In these embodiments, the primer has a capacity to bind any of the form of the nucleic acids, such as single stranded, double stranded or hetero duplex form for hybridization followed by nucleic acid synthesis.

Nucleotides useful in the inventive methods include both deoxyribonucleotides ("dNTPs") and ribonucleotides ("rNTPs"). The dNTP mixture provides a combination of deoxynucleotides required by a DNA polymerase for DNA synthesis. The dNTP mixture may include each of the naturally occurring deoxynucleotide bases (i.e., adenine (A), guanine (G), cytosine (C), and Thymine (T)). In some embodiments, each of the naturally occurring deoxynucleotides may be replaced or supplemented with a synthetic analog; provided however that deoxyinosinetriphosphate may not replace or supplement dGTP in the dNTP mixture.

In some embodiments, the synthesis reactions take place in a buffer that results in a reaction pH of between 6 and 9. In some embodiments, the pH is 7.7. Most art-recognized buffers for nucleic acid synthesis reactions (e.g., Tris buffers or HEPES buffers) may be employed.

In general, buffers that enhance DNA stability (e.g., HEPES) may be used in certain amplicon production methods. However, Tris:Borate, HEPES, and MOPS buffers may be disfavored for some specific amplicon production methods employing thermal denaturation of a target DNA.

Polymerase enzymes typically require divalent cations (e.g., Mg+2, Mn+2, or combinations thereof). Accordingly, in certain embodiments, one or more divalent cations may be added to the reaction mixture. $MgCl_2$ may be added to the reaction mixture at a concentration range of 2 mM to 6 mM. Higher concentration of $MgCl_2$ is desirable when high concentration (e.g., greater than 10 pmoles, greater than 20 pmoles, or greater than 30 pmoles) of inosine-containing primer or primers is added to the reaction mixture.

In some embodiments, surfactants (e.g., detergents) may be added to the reaction mixture. In some embodiments, the surfactant is a detergent selected from Tween-20, NP-40, Triton-X-100, or combinations thereof. In some embodiments, 0.05% NP-40 and 0.005% Triton X-100 are added to the reaction mixture. Surfactants may be applied to the reaction tube before introducing the first component of the reaction mixture. Alternatively, surfactants may be added to the reaction mixture along with the reaction components. In some specific embodiments, the reaction buffer may comprise 25 mM Tris:borate; 5 mM $MgCl_2$; 0.01% Tween; and 20% ethylene glycol.

In some embodiments, one or more blocking agents such as an albumin (e.g., BSA) may be added to the reaction mixture to bind to the surface of the reaction vessel (e.g., plastic microcentrifuge tube or microtiter plate) increasing the relative amount target nucleic acid that is available for reaction with the reverse transcriptase, nucleases or polymerases.

In some embodiments, one or more reducing agents (e.g., DTT, βME, TCEP, or MEA) may be added to the reaction mixture to reduce oxidation of the enzymes in the reaction mix and improve the quality and yield of the amplicons produced.

In one or more embodiments, a kit for amplifying an RNA template, comprises at least one inosine-containing primer, and at least one enzyme, wherein the enzyme comprises a reverse transcriptase activity, a strand displacement DNA polymerase activity, a nuclease activity for nicking DNA 3' to an inosine residue of the primer and combinations thereof.

In one or more embodiments, the RNA template is isolated from eukaryotic origin, prokaryotic origin, viral origin, bacteriophage origin, or synthetic origin. The RNA template to be amplified can be isolated from various sources or various biological samples. The biological sample may be obtained from a biological subject that contains or is suspected of containing target nucleic acids. A biological sample also includes samples from a region of a biological subject containing diseased cells. A biological sample may be of eukaryotic origin, for example, insects, protozoa, birds, fish, reptiles, and preferably a mammal, for example, rat, mouse, cow, dog, guinea pig, or rabbit, or a primate, for example, chimpanzees or humans. Alternatively, a biological sample may be of prokaryotic origin or viral or bacteriophage origin.

In one embodiment of the kit, at least one enzyme has reverse transcriptase activity, at least one enzyme has strand displacement DNA polymerase activity, and at least one enzyme has a nuclease activity for nicking DNA 3' to an inosine residue of the primer. In some other embodiments, at least one enzyme has both of the reverse transcriptase and strand displacement DNA polymerase activity. In some other embodiments, at least one enzyme has a reverse transcriptase, strand displacement DNA polymerase activity and a nuclease activity for nicking DNA 3' to an inosine residue of the primer. In some embodiments, the DNA polymerase is an exonuclease deficient DNA polymerase. In another embodiment, the kit may comprise an enzyme, which has a reverse transcriptase activity and an exonuclease deficient strand displacement DNA polymerase activity. For example, delta Tts is a DNA polymerase that has reverse transcriptase activity. See, for example, U.S. Pat. No. 5,744,312. One or more embodiments of the kit may comprise the DNA polymerase selected from a Bst DNA polymerase, an exonuclease deficient T7 DNA polymerase, exo (−) Klenow, delta Tts DNA polymerase and combinations thereof.

In one embodiment, the kit comprises an endonuclease V. In some specific embodiments, the endonuclease V is selected from a protein with a sequence of SEQ ID NO: 25, SEQ ID NO: 26, SEQ ID NO: 27 or conservative variants thereof.

In some embodiments, the kit further comprises dNTPs, buffer, SSB, reducing agents, denaturing agent, blocking agents, surfactants and combinations thereof. The concentration of the dNTPs comprising dTTP. dCTP. dATP and dGTP is in a range of about 100 µM to 100,000 µM. The kit may further comprise buffer, which is selected from Tris, HEPES or MOPS. The kit may comprise one or more surfactants, which is selected from Tween-20, NP-40, Triton X-100 and combinations thereof.

In one or more embodiments, the kit further comprises one or more reducing agents, which are selected from dithiothreitol (DTT). 2-mercaptoethanol (β-ME). 2-mercaptoethylamine (MEA), Tris(carboxyethyl)phosphine (TCEP).

The kit may further comprise a single stranded DNA binding protein, which is selected from E. coli SSB, T4 gene 32 protein, T7 gene 2.5 protein, Ncp7, recA and combinations thereof. The kit may comprise a blocking agent comprising an albumin. The kit may further comprise at least one topoisomerase, may be selected from type I topoisomerase.

Figure 1:
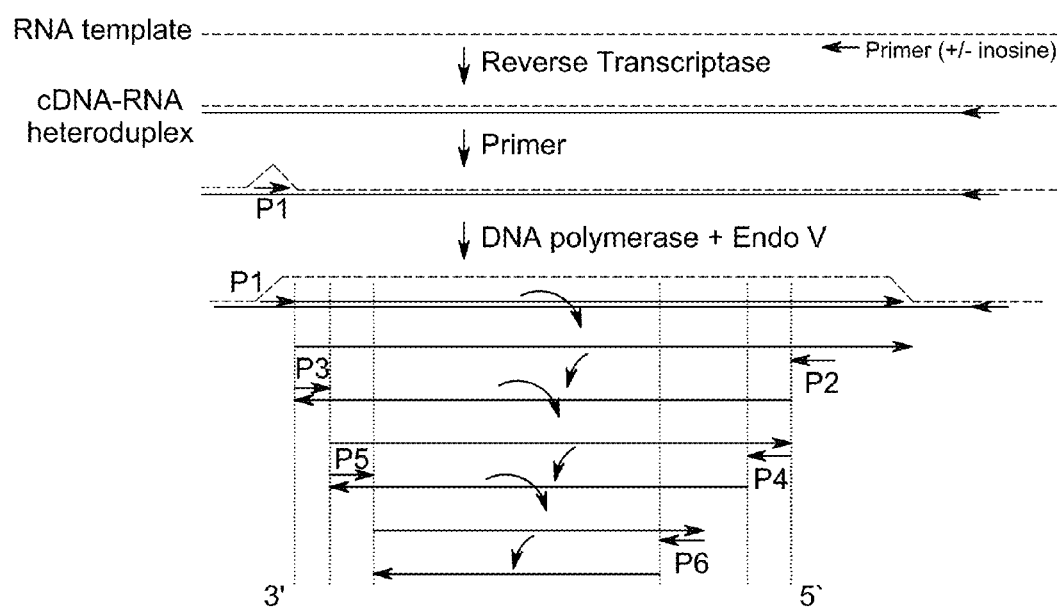
FIG. 1 is a schematic representation of an example of a DNA synthesis scheme starting from an RNA template via a cDNA:RNA heteroduplex intermediate.

An exemplary embodiment of RNA amplification is schematically represented by FIG. 1. The FIG. 1 illustrates formation of cDNA:RNA heteroduplex by reverse transcription of RNA template, followed by DNA amplification. The amplification reaction starts when the nucleotide analog containing primer, such as inosine-containing primer binds to the cDNA template, displacing the RNA from the heteroduplex, as shown in FIG. 1. After binding of a forward primer to the cDNA template, the endonuclease forms a nick 3' to the inosine-containing forward primer and DNA polymerase synthesizes a complementary strand of DNA. The process of producing a complementary strand of DNA is referred to as extension. This nicking and subsequent extension occurs repeatedly in a cyclic fashion, thereby producing amplification products of the template strand. This step is followed by multiple amplification reactions using a plurality of forward and reverse primer, including P1, P2, P3, P4, P5, P6 which binds to 3' or 5' end of the template DNA, and in the same mechanism results in formation of amplified product.

Figure 2:
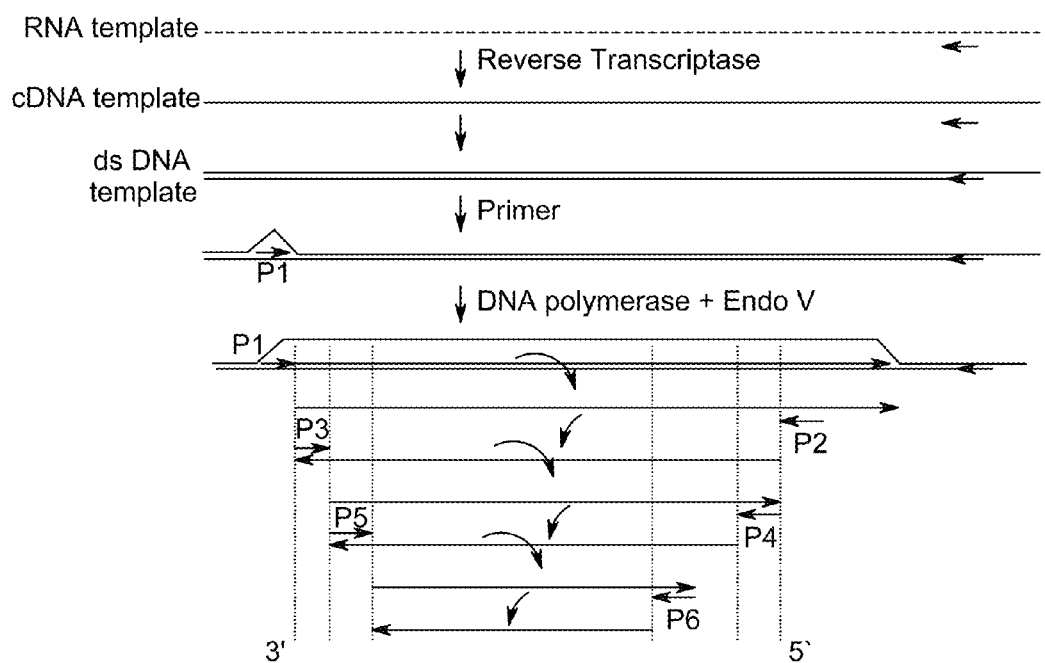
FIG. 2 is a schematic representation of a DNA synthesis scheme starting from an RNA template via a double-stranded DNA intermediate.

FIG. 2 illustrates another exemplary embodiment of DNA amplification starting from a RNA template, in a schematic representation. In this embodiment, the cDNA is generated by reverse transcription of RNA template, followed by DNA amplification. The single stranded cDNA forms a double stranded DNA by synthesizing a complementary strand using DNA polymerase and at least a primer. The amplification reaction starts when the inosine-containing primer binds to the cDNA template, displacing the complementary DNA strand, as shown in FIG. 2. Using endonuclease, the inosine-containing forward and reverse primers including P1, P2, P3, P4, P5, P6 and DNA polymerase, multiple amplification reactions proceeds to generate amplified product.

FIG. 3 illustrates schematically the nick formation and strand displacing amplification reaction, wherein the amplification reaction starts when the primer contains modified bases, such as inosine-containing primer binds to the cDNA template. After binding of a forward primer to the cDNA template, the endonuclease forms a nick to the inosine-containing forward primer forming a nick on the primer strand. The strand displacing DNA polymerase then binds to the 3' end of the primer at the nick, and synthesizes complementary strand of the template DNA in 5' to 3' direction. This step is followed by multiple nick formation and amplification reactions using a plurality of forward and reverse primers to form amplified product.

The basic method shown in FIG. 3 may be varied by employing additional primers or other oligonucleotides, additional enzymes, additional nucleotides, stains, dyes, or other labeled components. Thus, for example, amplification with a single primer may be used for dideoxy sequencing, producing multiple sequencing products for each molecule of template, and, optionally by the addition of dye-labeled dideoxynucleotide terminators. Labeled probes may be generated from double-stranded cDNA made with a sequence-tagged oligo (dT) primer from mRNA samples. A single primer may be the complement of the tag sequence, facilitating identification and/or isolation.

Amplification with multiple, paired primers facilitates rapid and extensive amplification, which is useful to detect the presence of specific sequences, to quantify the amounts of those sequences present in a sample, or to produce quantities of a sequence for analysis by methods such as electrophoresis for size measurement, restriction enzyme digestion, sequencing, hybridization, or other molecular biological techniques.

Example 1 DNA Amplification Starting from RNA Template Irrespective of Denaturation Conditions FirstChoice® Human Spleen Total RNA was obtained from Life Technologies™. Oligos were obtained from Integrated DNA Technologies, Inc. The cDNA:RNA heteroduplex was prepared from total spleen RNA using Oligo SEQ ID NO: 1 with SuperScript® II (SS II) reverse transcriptase and accompanying buffer was purchased from Life Technologies™ and prepared according to the manufacturer's instructions.

TABLE 1

Oligonucleotides sequences used for example 1.

| SEQ. ID No. | Oligonucleotide Sequence |
|---|---|
| 1 | 5'-d[CCAGCCTGGGCATCCTTGAI*T]-3' |
| 2 | 5'-d[TTCAGCTCTCGGAACATCTCI*A]-3' |
| 3 | 5'-d[TCACGCCCACGGATCTGAAI*G]-3' |
| 4 | 5'-d[CATCCAGTGGTTTCTTCTTTI*G]-3' |
| 5 | 5'-d[GAGAGGAGCTGGTGTTGTTI*G]-3' |
| 6 | 5'-d[TGCTCGCTTAGTGCTCCCTI*G]- 3' |
| 7 | 5'-d[TTGTGCCTGTCCTGGGAGAI*A]-3' |
| 8 | 5'-d[GACGGAACAGCTTTGAGGTI*C]-3' |
| 9 | 5'-d[CACACTGGAAGACTCCAGTI*G]-3' |
| 10 | 5'-d[TGGGCGGCATGAACCGGAI*G]-3' |
| 11 | 5'-d[CTACATGTGTAACAGTTCCTI*C]-3' |
| 12 | 5'-d[CCTGAGGTTGGCTCTGACTI*T]-3' |

Table 1 contains oligos of SEQ ID No's 1-12, wherein "I" represents inosine and "*" represents phosphorothioate linkage in the oligo sequences. A reaction mixture (mix) was prepared with oligos of SEQ ID No's 1-12 in 0.01% Tween 20 (Sigma) so that 1 µl of the mix contained 10 pmol of each oligo (Oligo Mix). 10× Denaturation buffer was a combination of 100 mM HEPES (Sigma), pH 8.0, 1 mM EDTA (Life Technologies) and 0.1% Tween 20 (Sigma). 10× Reaction Buffer was a combination of 100 mM HEPES, pH 8.0, 30 mM magnesium chloride (Life Technologies), 1 mM manganese sulphate (Sigma), 0.1% Tween 20, 2.5 mM dATP (GE Healthcare), 2.5 mM dCTP (GE Healthcare), 2.5 mM dGTP (GE Healthcare), 2.5 mM dTTP (GE Healthcare) and 100 mM DTT (Sigma). Enzyme dilution buffer was 10 mM HEPES, pH 8.0, 1 mM DTT, 0.1 mM EDTA, 200 mM sodium chloride (Sigma), 0.01% Tween 20 and 50% glycerol (Sigma). The large fragment of Bst DNA polymerase (DNAP) was from New England Biolabs®, Inc. Mutant *Escherichia coli* endonuclease V (Endo V; Y76A) was from General Electric Company. Additional reagents included 25% formamide (Sigma) and 99.5% ethylene glycol (Sigma).

A single isothermal amplification reaction was prepared with a final volume of 10 µl. 5 µl of this total volume was from the denaturation mix and 5 µl was from the reaction mixture.

The denaturation mix contained either 200 ng total spleen RNA or 1 µl of the completed cDNA reaction. 0.5 µl of 10× denaturation buffer, 0.5 µl of 25% formamide and 1 µl of the Oligo mix was added to the denaturation mix and the final volume was adjusted to 5 µl with water. When a no template control (NTC) was included, the volume of cDNA or total RNA was replaced with water (GIBCO®).

Each enzyme mix consisted of 40 units of Bst DNA polymerase, 1 µg *Escherichia coli* single strand DNA binding protein (SSB; Affymetrix-USB) and 255 ng of Endo V (Y76A). The final volume of enzyme mix was adjusted to 1 µl with Enzyme Dilution Buffer. The enzyme mix (1 µl) was then combined with 1 µl 10× Reaction Buffer, 2 µl ethylene glycol and 1 µl 10 mg/ml BSA (Sigma) to prepare the Reaction Mixture.

For this example, two identical sets containing six reactions each were prepared. Reaction 1 was the No Template Control (NTC), reaction 2 contained 1 µl of cDNA along with Bst DNAP, reaction 3 contained 200 ng of RNA along with Bst DNAP, reaction 4 contained 200 ng of RNA along with both Bst DNAP and SS II, reaction 5 contained RNA along with Bst DNAP with 75 mM KCl added and reaction 6 contained RNA along with both Bst DNAP and SS II with 75 mM KCl added.

TABLE 2

Composition of different reaction mixture.

| Reagents | Reaction mixture | | | | | |
|---|---|---|---|---|---|---|
| | 1 (NTC) | 2 | 3 | 4 | 5 | 6 |
| Denaturation mix with RNA | – | – | 200 ng | 200 ng | 200 ng | 200 ng |
| Denaturation mix with cDNA | – | 1 µl | – | – | – | – |
| Reaction mix with Bst DNAP | + | + | + | + | + | + |
| SS ™ II (RT) | – | – | – | + | – | + |
| 75 mM KCl | – | – | – | – | + | + |

One set of Denaturation Mix sample was treated by heating at 65° C. for five minutes and then cooling to 22° C. The other set of Denaturation Mix sample was denatured by heating at 95° C. for two minutes and then cooling to 22° C. After cooling, each sample was vortexed and microfuged.

The separate Denaturation Mix and Reaction Mix were preheated at 45° C. for 30 seconds before mixing 5 µl of the Reaction Mix with 5 µl of the Denaturation Mix. The reactions were incubated at 45° C. for one hour. Following the incubation, 3 µl from each reaction were mixed with 6 µl of Gel Loading Buffer II (Life Technologies), heat denatured at 95° C. for two minutes and quenched on ice. Five microliters from each denaturation sample was loaded into separate wells of a 10% acrylamide TBE-Urea gel (Life Technologies, Inc.) and electrophoresis was performed according to the manufacturer's instructions.

Included on the gel was one lane containing 0.45 µg of a 10 bp DNA Ladder (Life Technologies; Lane M). Electrophoresis was continued until the bromophenol blue dye was approximately 2 cm from the bottom of the gel. The gel was stained for 15 minutes in a 1:500 dilution of SYBR Gold (Life Technologies) in TE Buffer, pH 7.4 (Sigma), and imaged on a Typhoon™ 9410 Variable Mode Imager (GE Healthcare).

FIG. 4 shows the image of the gel, wherein the bands of expected size is appeared in both reaction 2, which used cDNA as a template for amplification and reaction 4, which used total RNA as a template for amplification and mixed with Bst DNA polymerase and SSII reverse transcriptase. The bands in lanes 2 and 4 are same for both with and without an initial denaturation at 95° C., demonstrating the isothermal amplification method worked when starting from an RNA template in a single tube. The isothermal amplification occurs in one step reaction starting from RNA template, where RNA converted to cDNA using SSII™ RT before or after denaturation at 95° C. There is no amplified product shown in lanes 1, 3, 5 and 6. The absence of any amplified product in lane 1, as NTC is expected as the reaction mixture was devoid of any template. The absence of amplified product in lane 3, where the reaction mixture contained RNA and Bst DNA Pol, determines that RNA was not converted to cDNA in presence of Bst DNA Pol and therefore the enzyme Bst DNA Pol does not have any reverse transcriptase activity. Lane 5 showed no amplified product in absence of reverse transcriptase, and the Bst DNA Pol was not able to reverse transcribe RNA even in presence of 75 mM KCl. Lane 6 showed lowest concentration of amplified product, wherein the reaction was performed in presence of RNA, Bst DNA Pol, SSII and 75 mM KCl. As the reaction mixture of lane 6 is different than the reaction mixture of lane 4 only by addition of 75 mM KCl in reaction 6. Ideally KCl is used to optimize a reverse transcription reaction, though higher concentration of KCl seems to have an inhibitory effect on the endonuclease V, thereby inhibit the entire reaction.

Example 2 Reverse Transcription Using Different Reverse Transcriptase Enzymes

Isothermal amplification reactions were prepared and analyzed as Example 1 with denaturation of the starting RNA template carried out at 95° C. For this example, increasing amount of either Moloney Murine Leukemia Virus (MMLV; Life Technologies) reverse transcriptase (RTase) which contains both reverse transcriptase and RNAse H activities, or SS II RTase (decreased RNAse H activity) were added to the amplification reactions. Where indicated, reactions contained 12.5, 25, 50 or 100 units of either MMLV or SS II. Amplification reactions containing either of the RTases synthesized fragments of expected sizes, indicating successful amplification of the target mRNA in the single combined reaction of RNA reverse transcription followed by amplification, as shown in FIG. 5.

Example 3 Isothermal Amplification of RNA in a Single Reaction Mixture without Denaturation Isothermal amplification reactions were prepared and analyzed as Example 1 but without any denaturation of the starting RNA template prior to amplification. 200 ng of total RNA (from spleen or kidney) was amplified separately with or without a 30 minute pretreatment with RNase A (to eliminate the RNA, as a negative control). The oligo mix was the same one used previously in Example 1 that had amplified the correct product sizes starting from a cDNA: RNA template. The RNase A was not inactivated prior to amplification. Fifty units of SS II were included in all reactions.

TABLE 3

Oligonucleotides sequences used for example 3

| SEQ. ID No. | Oligonucleotide Sequence |
|---|---|
| 13 | 5'-d[GCCTCAGCCTCCCGAI*T]-3' |
| 14 | 5'-d[CTGGGATTACAGGCATI*C]-3' |
| 15 | 5'-d[CTCCCGGGTTCAAGCI*A]-3' |
| 16 | 5'-d[GAGATCTCAGCTCACCI*C]-3' |
| 17 | 5'-d[CAGGCTGGAGTGTAATI*G]-3' |
| 18 | 5'-d[GACGGAGTTTCACTCTTI*T]-3' |
| 19 | 5'-d[CTGAGGTCGGGAGTTTI*A]-3' |
| 20 | 5'-d[GAGGCCAAGGCGAGTI*I]-3' |
| 21 | 5'-d[GGCGCAGTGGCTCACI*A]-3' |
| 22 | 5'-d[AAAATGGGGTAAGGGGI*C]-3' |

TABLE 3-continued

Oligonucleotides sequences used for example 3

| SEQ. ID No. | Oligonucleotide Sequence |
|---|---|
| 23 | 5'-d[ACCCCCGTCAAACTCAI*T]-3' |
| 24 | 5'-d[GTCATATACTCAGCCCTI*C]-3' |

Table 3 contains oligos of SEQ ID No's 13-24, wherein "I" represents inosine and "*" represents phosphorothioate linkage in the oligo sequences. Human genomic DNA was amplified under identical conditions using a different primer set (Oligo SEQ ID NO: 13-24) designed to amplify p53 as a positive control for amplification. Amplification controls included: 1) no template/no enzymes (NE) and, 2) no template/plus enzymes (NTC). The FIG. 6 shows bands of expected sizes for RNA amplification from both the spleen and kidney RNA as starting material without RNase A treatment. The FIG. 6 shows the lower amount of amplification products from the RNA template isolated from kidney compared to the RNA template isolated from spleen establishes that a lower copy number of p53 mRNA in the kidney as expected. Additionally FIG. 6 shows, the DNA amplification produces fragments of expected sizes with or without RNase treatment even with reverse transcriptase present in the reaction. FIG. 7 shows amplification product of RNA template treated with RNase A. RNase A treatment of the templates prior to amplification does not show the expected amplification products, suggesting that amplification occurs from an RNA template in a single tube. The results of this experiment demonstrates 1) that a heat denaturation of the starting material is not required for a successful single tube amplification reaction (RNA or DNA), and 2) a single amplification formula for amplification from DNA or RNA in a single tube can be used in amplification of the present invention.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An isothermal method for generating an amplified cDNA from an RNA template in a single tube, the method comprising:
   (a) providing the RNA template;
   (b) reverse transcribing the RNA template under an isothermal condition to generate a cDNA:RNA heteroduplex by incubating the RNA template with a reaction mixture comprising at least one primer capable of hybridizing to the RNA template, a reverse transcriptase with reduced RNAse H activity, and deoxynucleoside triphosphates (dNTPs); and
   (c) amplifying the cDNA of the cDNA:RNA heteroduplex under the same isothermal condition to form the amplified cDNA by incubating the reaction mixture of step (b) with an amplification reaction mixture comprising at least one strand displacement DNA polymerase, at least one inosine-containing primer capable of hybridizing to the cDNA strand of the cDNA:RNA heteroduplex, an endonuclease capable of nicking a double stranded DNA 3' to an inosine residue, deoxynucleoside triphosphates (dNTPs), glycerol, formamide, and ethylene glycol,
   wherein the amplification reaction mixture has a low salt concentration to allow the at least one inosine-containing primer to hybridize with the cDNA:RNA heteroduplex without heat-denaturation of the cDNA:RNA heteroduplex, and
   wherein the steps (a)-(c) are performed in the single tube under the said isothermal condition at a temperature in a range from about 40° C. to about 50° C.

2. The method of claim 1, wherein the at least one primer capable of hybridizing to the RNA template comprises an oligo (Dt) primer, a Locked Nucleic Acid (LNA), a Peptide Nucleic Acid (PNA) or combinations thereof.

3. The method of claim 1, wherein the amplified cDNA is complementary to at least a portion of the cDNA of the cDNA:RNA heteroduplex.

4. The method of claim 1, wherein the amplification reaction mixture of step (c) comprises multiple forward and reverse inosine-containing primers capable of hybridizing to the cDNA strand of the cDNA:RNA heteroduplex.

5. The method of claim 1, wherein the reverse transcriptase with reduced RNAse H activity is selected from one or more of a mutated form of MMLV reverse transcriptase, a mutated form of AMY reverse transcriptase, a mutated form of HIV reverse transcriptase, or conservative variants thereof.

6. The method of claim 1, wherein at least one inosine nucleotide of the at least one inosine-containing primer is positioned at least 4 nucleotides from the 5' end of the at least one inosine-containing primer.

7. The method of claim 1, wherein the at least one inosine-containing primer comprises a phosphorothioate linkage.

8. The method of claim 1, wherein the amplification reaction mixture comprises at least one extender template.

9. The method of claim 1, wherein the at least one inosine-containing primer has a sequence length ranging between 5 to 100, 5 to 30, or 5 to 20 nucleotides.

10. The method of claim 1, wherein the at least one strand displacement DNA polymerase is an exonuclease deficient polymerase.

11. The method of claim 1, wherein the at least one strand displacement DNA polymerase is selected from a group consisting of Bst DNA polymerase, an exonuclease deficient T7 DNA polymerase, exo (−) Klenow, delta Tts DNA polymerase, BCA DNA polymerase, Phi 29 DNA polymerase, T4 DNA polymerase, T5 DNA polymerase and combinations thereof.

12. The method of claim 1, wherein the endonuclease is an endonuclease V.

13. The method of claim 12, wherein the endonuclease V is selected from a protein with a sequence of SEQ ID NO: 25, SEQ ID NO: 26, SEQ ID NO:27 or conservative variants thereof.

14. The method of claim 1, wherein a final concentration of the dNTPs comprising dTTP, dCTP, dATP and dGTP in the reaction mixture is in a range of about 10 µM to 10,000 µM.

15. The method of claim 1, wherein the amplification reaction mixture further comprises a surfactant.

16. The method of claim 1, wherein the amplification reaction mixture further comprises a divalent cation selected from $Mn^{2+}$, $Mg^{2+}$ or a combination thereof.

17. The method of claim 1, wherein the amplification reaction mixture further comprises a reducing agent selected from dithiothreitol (DTT), 2-mercaptoethanol (β-ME), 2-mercaptoethylamine (MEA), or Tris(carboxyethyl) phosphine (TCEP).

18. The method of claim 1, wherein the amplification reaction mixture further comprises at least one single stranded DNA binding protein (SSB).

19. The method of claim 18, wherein the at least one single stranded DNA binding protein is selected from a group consisting of E. coli SSB, T4 gene 32 protein, T7 gene 15 protein, Ncp7, recA and combinations thereof.

20. The method of claim 1, wherein the RNA template is isolated from eukaryotic origin, prokaryotic origin, viral origin, bacteriophage origin, or synthetic origin.

21. The method of claim 1, wherein the reverse transcriptase with reduced RNAse H activity is a mutated form of MMLV reverse transcriptase.

22. The method of claim 1, further comprising quantifying the RNA template by measuring the rate of amplification of the cDNA.

* * * * *